United States Patent
Wan et al.

(10) Patent No.: US 11,427,635 B2
(45) Date of Patent: Aug. 30, 2022

(54) CD47 SINGLE-DOMAIN ANTIBODY AND USE THEREOF

(71) Applicant: SHANGHAI NOVAMAB BIOPHARMACEUTICALS CO., LTD., Shanghai (CN)

(72) Inventors: Yakun Wan, Shanghai (CN); Xiaoning Shen, Shanghai (CN); Min Zhu, Shanghai (CN)

(73) Assignee: SHANGHAI NOVAMAB BIOPHARMACEUTICALS CO., LTD., Shanghai (CN)

( * ) Notice: Subject to any disclaimer, the term of this patent is extended or adjusted under 35 U.S.C. 154(b) by 220 days.

(21) Appl. No.: 16/763,052

(22) PCT Filed: Nov. 16, 2018

(86) PCT No.: PCT/CN2018/116006
§ 371 (c)(1),
(2) Date: May 11, 2020

(87) PCT Pub. No.: WO2019/157843
PCT Pub. Date: Aug. 22, 2019

(65) Prior Publication Data
US 2020/0385465 A1     Dec. 10, 2020

(30) Foreign Application Priority Data
Feb. 14, 2018   (CN) .......................... 201810151752.6

(51) Int. Cl.
*C07K 16/28*   (2006.01)
*A61P 35/00*   (2006.01)
*A61K 39/00*   (2006.01)

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/565* (2013.01); *C07K 2317/569* (2013.01); *C07K 2317/76* (2013.01); *C07K 2317/94* (2013.01)

(58) Field of Classification Search
CPC ............ C07K 16/2803; C07K 2317/24; C07K 2317/565; C07K 2317/569; A61P 35/00; A61K 2039/505
See application file for complete search history.

*Primary Examiner* — Joanne Hama
*Assistant Examiner* — Miles Joseph Delahoussaye
(74) *Attorney, Agent, or Firm* — Novick, Kim & Lee, PLLC; Zhi Yang Xue; Bin Lu

(57) ABSTRACT

A CD47 single-domain antibody and use thereof, and in particularly, a blocking type single-domain antibody for integrin-related protein (CD47) and derivative proteins thereof. In particular, disclosed are an integrin-related protein (CD47) binding molecule and use thereof, particularly in the treatment and/or prevention, or diagnosis of CD47-associated diseases, such as tumors. The CD47 single-domain antibody involved can effectively block the interaction between CD47 and a ligand SIRPa thereof, has good binding activity, blocking activity, affinity and stability, can effectively enhance the phagocytosis of tumor cells by macrophages, and shows significant anti-tumor activity in both a human lymphoma model and a human ovarian cancer model. In addition, the antibody does not cause hemoagglutination in vitro, and shows excellent safety in cynomolgus monkeys.

16 Claims, 11 Drawing Sheets
Specification includes a Sequence Listing.

SEQUENCE LISTING

```
<160> NUMBER OF SEQ ID NOS: 18

<210> SEQ ID NO 1
<211> LENGTH: 25
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR1

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Ala Ala Ser
            20                  25

<210> SEQ ID NO 2
<211> LENGTH: 15
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR2

<400> SEQUENCE: 2

Trp Phe Arg Gln Thr Pro Gly Lys Glu Arg Glu Gly Val Ala Leu
1               5                   10                  15

<210> SEQ ID NO 3
<211> LENGTH: 38
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR3

<400> SEQUENCE: 3
```

-continued

```
Asn Tyr Ala Asp Ser Val Lys Gly Arg Phe Thr Ile Ser Gln Asp Asn
1               5                   10                  15

Val Lys Asn Thr Val Tyr Leu Gln Met Asn Ser Leu Lys Pro Glu Asp
            20                  25                  30

Thr Ala Met Tyr Tyr Cys
        35

<210> SEQ ID NO 4
<211> LENGTH: 11
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR4

<400> SEQUENCE: 4

Trp Gly Gln Gly Thr Gln Val Thr Val Ser Ser
1               5                   10

<210> SEQ ID NO 5
<211> LENGTH: 10
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: CDR1

<400> SEQUENCE: 5

Gly Tyr Ala Tyr Thr Ser Asp Cys Met Gly
1               5                   10

<210> SEQ ID NO 6
<211> LENGTH: 8
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: CDR2

<400> SEQUENCE: 6

Ile Tyr Thr Pro Gly Asn Ser Thr
1               5

<210> SEQ ID NO 7
<211> LENGTH: 15
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: CDR3

<400> SEQUENCE: 7

Ala Ala Arg Arg Gly Ala Cys Ser Leu Arg Leu Pro Phe Phe Tyr
1               5                   10                  15

<210> SEQ ID NO 8
<211> LENGTH: 122
<212> TYPE: PRT
<213> ORGANISM: artificial sequence
<220> FEATURE:
```

<223> OTHER INFORMATION: synthesized
<220> FEATURE:
<221> NAME/KEY: misc_feature
<223> OTHER INFORMATION: complete amino acid sequence

<400> SEQUENCE: 8

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ala Tyr Thr Ser Asp
            20                  25                  30

Cys Met Gly Trp Phe Arg Gln Thr Pro Gly Lys Glu Arg Glu Gly Val
        35                  40                  45

Ala Leu Ile Tyr Thr Pro Gly Asn Ser Thr Asn Tyr Ala Asp Ser Val
    50                  55                  60

Lys Gly Arg Phe Thr Ile Ser Gln Asp Asn Val Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Arg Gly Ala Cys Ser Leu Arg Leu Pro Phe Phe Tyr Trp
            100                 105                 110

Gly Gln Gly Thr Gln Val Thr Val Ser Ser
        115                 120
```

<210> SEQ ID NO 9
<211> LENGTH: 366
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: complete nucleotide sequence

<400> SEQUENCE: 9

```
caggtgcagc tgcaggagtc tgggggaggc tcggtgcagg ctggagggtc tctgagactc      60
tcctgtgcag cctctggata cgcctacact agcgactgca tgggctggtt ccgccagact     120
ccagggaagg agcgcgaggg ggtcgcactt atttatacgc ctggtaatag cacaaactat     180
gccgactccg tgaagggtcg attcaccatc tcccaagaca cgtcaagaa cacggtgtat     240
ctgcaaatga acagcctgaa acctgaggac actgccatgt actactgtgc ggcgagacga     300
ggcgcctgct cacttaggtt gcccttttttt tactggggcc aggggaccca ggtcaccgtc     360
tcctca                                                                366
```

<210> SEQ ID NO 10
<211> LENGTH: 25
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR1

<400> SEQUENCE: 10

```
Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 11

```
<211> LENGTH: 15
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR2

<400> SEQUENCE: 11

Trp Phe Arg Gln Thr Pro Gly Lys Gly Leu Glu Gly Val Ala Leu
1               5                   10                  15

<210> SEQ ID NO 12
<211> LENGTH: 38
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR3

<400> SEQUENCE: 12

Asn Tyr Ala Asp Ser Val Lys Gly Arg Phe Thr Ile Ser Gln Asp Asn
1               5                   10                  15

Ser Lys Ser Thr Val Tyr Leu Gln Met Asn Ser Leu Arg Ala Glu Asp
            20                  25                  30

Thr Ala Met Tyr Tyr Cys
        35

<210> SEQ ID NO 13
<211> LENGTH: 11
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: FR4

<400> SEQUENCE: 13

Trp Gly Gln Gly Thr Leu Val Thr Val Ser Ser
1               5                   10

<210> SEQ ID NO 14
<211> LENGTH: 122
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: complete amino acid sequence

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ala Tyr Thr Ser Asp
            20                  25                  30

Cys Met Gly Trp Phe Arg Gln Thr Pro Gly Lys Gly Leu Glu Gly Val
        35                  40                  45

Ala Leu Ile Tyr Thr Pro Gly Asn Ser Thr Asn Tyr Ala Asp Ser Val
    50                  55                  60

Lys Gly Arg Phe Thr Ile Ser Gln Asp Asn Ser Lys Ser Thr Val Tyr
65                  70                  75                  80
```

Leu Gln Met Asn Ser Leu Arg Ala Glu Asp Thr Ala Met Tyr Tyr Cys
                85                  90                  95

Ala Ala Arg Arg Gly Ala Cys Ser Leu Arg Leu Pro Phe Phe Tyr Trp
            100                 105                 110

Gly Gln Gly Thr Leu Val Thr Val Ser Ser
        115                 120

<210> SEQ ID NO 15
<211> LENGTH: 366
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: complete nucleotide sequence

<400> SEQUENCE: 15
caggtgcagc tgcaggagtc cggcggcggc ctggtgcagc ccggcggctc cctgaggctg      60
tcctgcgccg cctccggcta cgcctacacc tccgactgca tgggctggtt caggcagacc     120
cccggcaagg gcctggaggg cgtggccctg atctacaccc ccggcaactc caccaactac     180
gccgactccg tgaagggcag gttcaccatc tcccaggaca actccaagtc caccgtgtac     240
ctgcagatga actccctgag ggccgaggac accgccatgt actactgcgc cgccaggagg     300
ggcgcctgct ccctgaggct gcccttcttc tactggggcc agggcaccct ggtgaccgtg     360
tcctcc                                                                366

<210> SEQ ID NO 16
<211> LENGTH: 351
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: fusion protein

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ala Tyr Thr Ser Asp
            20                  25                  30

Cys Met Gly Trp Phe Arg Gln Thr Pro Gly Lys Gly Leu Glu Gly Val
        35                  40                  45

Ala Leu Ile Tyr Thr Pro Gly Asn Ser Thr Asn Tyr Ala Asp Ser Val
    50                  55                  60

Lys Gly Arg Phe Thr Ile Ser Gln Asp Asn Ser Lys Ser Thr Val Tyr
65                  70                  75                  80

Leu Gln Met Asn Ser Leu Arg Ala Glu Asp Thr Ala Met Tyr Tyr Cys
                85                  90                  95

Ala Ala Arg Arg Gly Ala Cys Ser Leu Arg Leu Pro Phe Phe Tyr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Glu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Asp Val Ser Gln Glu Asp Pro Glu
            165                 170                 175

Val Gln Phe Asn Trp Tyr Val Asp Gly Val Glu Val His Asn Ala Lys
        180                 185                 190

Thr Lys Pro Arg Glu Glu Gln Phe Asn Ser Thr Tyr Arg Val Val Ser
    195                 200                 205

Val Leu Thr Val Leu His Gln Asp Trp Leu Asn Gly Lys Glu Tyr Lys
210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
            245                 250                 255

Pro Ser Gln Glu Glu Met Thr Lys Asn Gln Val Ser Leu Thr Cys Leu
        260                 265                 270

Val Lys Gly Phe Tyr Pro Ser Asp Ile Ala Val Glu Trp Glu Ser Asn
    275                 280                 285

Gly Gln Pro Glu Asn Asn Tyr Lys Thr Thr Pro Pro Val Leu Asp Ser
290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
            325                 330                 335

His Asn His Tyr Thr Gln Lys Ser Leu Ser Leu Ser Leu Gly Lys
        340                 345                 350

<210> SEQ ID NO 17
<211> LENGTH: 1053
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: codon optimized base sequence

<400> SEQUENCE: 17
caggtgcagc tgcaggagtc cggcggcggc ctggtgcagc ccggcggctc cctgaggctg      60
tcctgcgccg cctccggcta cgcctacacc tccgactgca tgggctggtt caggcagacc     120
cccggcaagg gcctggaggg cgtggccctg atctacaccc ccggcaactc caccaactac     180
gccgactccg tgaagggcag gttcaccatc tcccaggaca actccaagtc caccgtgtac     240
ctgcagatga actccctgag ggccgaggac accgccatgt actactgcgc cgccaggagg     300
ggcgcctgct ccctgaggct gcccttcttc tactggggcc agggcaccct ggtgaccgtg     360
tcctccgagt ccaagtacgg ccccccctgc cccccctgcc ccgcccccga gttcgagggc     420
ggccccctcg tgttcctgtt cccccccaag cccaaggaca ccctgatgat ctccaggacc     480
cccgaggtga cctgcgtggt ggtggacgtg tcccaggagg accccgaggt gcagttcaac     540
tggtacgtgg acggcgtgga ggtgcacaac gccaagacca gcccagggga ggagcagttc     600
aactccacct acagggtggt gtccgtgctg accgtgctgc accaggactg gctgaacggc     660
aaggagtaca agtgcaaggt gtccaacaag ggcctgccct cctccatcga gaagaccatc     720
tccaaggcca aggccagcc agggagccc aggtgtaca ccctgccccc ctcccaggag     780
gagatgacca gaaccaggt gtccctgacc tgcctggtga agggcttcta ccctccgac      840 atcgccgtgg agtgggagtc caacggccag cccgagaaca actacaagac caccccccc      900

-continued

```
gtgctggact ccgacggctc cttcttcctg tactccaggc tgaccgtgga caagtccagg    960
tggcaggagg gcaacgtgtt ctcctgctcc gtgatgcacg aggccctgca caaccactac   1020
acccagaagt ccctgtccct gtccctgggc aag                                1053
```

<210> SEQ ID NO 18
<211> LENGTH: 229
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: Fc fragment

<400> SEQUENCE: 18

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225
```

CD47 SINGLE-DOMAIN ANTIBODY AND USE THEREOF

TECHNICAL FIELD

The present invention belongs to the technical field of biomedicine or bio-pharmaceuticals, and relates to a blocking single-domain antibody directed against the extracellular segment of integrin-related protein (CD47) molecule and a derived protein thereof. The coding sequence, related preparation methods and uses thereof are also disclosed, especially the use for treatment and/or prevention, or diagnosis of CD47-related diseases such as tumors.

BACKGROUND

In recent years, antibody drugs have become a research hotspot in the field of global biomedicine in the 21st century with their unique advantages, and more and more antibody drugs have entered clinical trials. Blocking the interaction between CD47 and SIRPa by using anti-CD47 antibodies has the effect of targeted therapy. The three drugs currently in Phase I are Forty Seven's Hu5F9-G4, Celgene's CC-90002, and Trillium's TTI-621, respectively. Trillium's CD47 antibody project is a SIRPa-Fc fusion protein, which has a similar CD47 affinity (nM level) as Hu5F9-G4. SIRPa-Fc has a smaller molecular weight of about 80 kDa, which has a better penetration and tissue distribution compared to 150 kDa antibody molecules. The affinity of SIRPa-Fc for red blood cells is much lower than that of Hu5F9-G4, indicating that it may have better security.

However, traditional monoclonal antibodies which have a large molecular weight, are difficult to penetrate into tissues, and the manufacturing cycle of monoclonal antibodies is long, and the humanization is more difficult. Therefore, it is particularly important to find antibodies with smaller molecular weights. In addition to antigen-binding fragments (Fab), single-chain antibodies (scFv) and other small-molecule antibodies modified based on traditional monoclonal antibodies, there is a naturally found smallest antigen-binding fragment in the body of Camelidae and shark family in nature. This antibody was discovered by Muyldermans et al. from the Vrije Universiteit Brussel in 1989. They first discovered a heavy chain antibody when separating and detecting antibodies in camel serum. The antibody lacks two light chain CLs and the constant region CH1, consisting of only the N-terminal variable region (VHH), hinge region and two constant regions (CH1, CH2), and the variable region (VHH) is called a single domain antibody (nanobody). The molecular weight of a single domain antibody is only about 15 kDa. Its nano-scale molecular size and unique structure enable it a variety of characteristics that are superior to traditional antibodies, such as high stability, good water solubility, simple humanization, high targeting and strong penetration, etc. Because of the special structural properties, single domain antibodies have the advantages of both traditional antibodies and small molecule drugs, and almost perfectly overcome the shortcomings of traditional antibodies such as long development cycle, low stability, and harsh storage conditions and the like. This single domain antibody with a molecular weight of only 1/10 of conventional antibodies has gradually become a new force in the new generation of antibody diagnosis and treatment. Therefore, the application of single domain antibody technology in the development of CD47 therapeutic antibody drugs has broad prospects.

SUMMARY OF THE INVENTION

The technical problem to be solved by the present invention is to provide a single domain antibody directed against the extracellular segment of CD47, which can effectively block the interaction between CD47 and its ligand SIRPa, and has a good binding activity, blocking activity, affinity and stability, and can effectively enhance the phagocytosis of tumor cells by macrophages, and shows a very significant antitumor activity in both human lymphoma model and human ovarian cancer model. In addition, the antibody not only does not cause human erythrocyte agglutination in vitro, but also exhibits excellent safety in cynomolgus monkeys. The present invention also provides a coding sequence of the single domain antibody and the derivatives thereof, a preparation method, and a use in diagnosis and treatment thereof.

To achieve the above purposes, in a first aspect of the present invention, it provides a complementarity determining region CDR region of an anti-CD47 single domain antibody VHH chain, wherein the complementarity determining region CDR of the VHH chain is composed of CDR1 as shown in SEQ ID NO: 5 CDR2 as shown in SEQ ID NO: 6, and CDR3 as shown in SEQ ID NO: 7.

In another preferred embodiment, the CDR1, CDR2 and CDR3 are separated by the framework regions FR1, FR2, FR3 and FR4 of the VHH chain.

In a second aspect of the present invention, it provides a VHH chain of an anti-CD47 single domain antibody, wherein the VHH chain comprises a framework region FR and the complementarity determining region CDR according to the first aspect of the present invention, wherein the framework region FR consists of:

(a) FR1 as shown in SEQ ID NO: 1, FR2 as shown in SEQ ID NO: 2, FR3 as shown in SEQ ID NO: 3, and FR4 as shown in SEQ ID NO: 4; or (b) FR1 as shown in SEQ ID NO: 10, FR2 as shown in SEQ ID NO: 11, FR3 as shown in SEQ ID NO: 12, and FR4 as shown in SEQ ID NO: 13.

In another preferred embodiment, the VHH chain of the anti-CD47 single domain antibody is shown in SEQ ID NO: 8 or 14.

In a third aspect of the present invention, it provides an anti-CD47 single domain antibody, which is a single-domain antibody directed against the CD47 epitope and has a VHH chain of the amino acid sequence as shown in SEQ ID NO: 8 or SEQ ID NO: 14.

In a fourth aspect of the present invention, it provides an anti-CD47 single domain antibody Fc fusion protein, wherein the structure of the fusion protein from N-terminus to C-terminus is shown as formula Ia or Ib:

$$A\text{-}L\text{-}B \quad (Ia);$$

$$B\text{-}L\text{-}A \quad (Ib)$$

wherein,
A is the anti-CD47 single domain antibody of claim 3;
B is a Fc fragment of IgG; and
L is none or a flexible linker.

In another preferred embodiment, the flexible linker is a peptide linker.

In another preferred embodiment, the peptide linker has 1-50 amino acids, preferably 1-20 amino acids.

In another preferred embodiment, the peptide linker has a structure of (GGGGS)n, wherein n is a positive integer of 1-5.

In another preferred embodiment, the Fc fragment of IgG comprises the Fc fragment of human IgG.

In another preferred embodiment, the Fc fragment of IgG is selected from the group consisting of: Fc fragments of IgG1, IgG2, IgG3, IgG4, and a combination thereof.

In another preferred embodiment, the Fc fragment of IgG is hIgG4PE.

In another preferred embodiment, the amino acid sequence of the Fc fragment is SEQ ID NO: 18.

In another preferred embodiment, the amino acid sequence of the fusion protein is shown in SEQ ID NO: 16.

In another preferred embodiment, the fusion protein is a single domain antibody Fc fusion protein directed against the CD47 epitope.

In a fifth aspect of the present invention, it provides a polynucleotide encoding a protein selected from the group consisting of: the CDR region of the anti-CD47 single domain antibody VHH chain according to the first aspect of the present invention, the VHH chain of the anti-CD47 single domain antibody according to the second aspect of the present invention, the anti-CD47 single domain antibody according to the third aspect of the present invention, and the anti-CD47 single domain antibody Fc fusion protein according to the fourth aspect of the present invention.

In another preferred embodiment, the polynucleotide has a nucleotide sequence as shown in SEQ ID NO: 9, 15, or 17.

In another preferred embodiment, the polynucleotide comprises DNA or RNA.

In a sixth aspect of the present invention, it provides an expression vector containing the polynucleotide according to the fifth aspect of the present invention.

In a seventh aspect of the present invention, it provides a host cell containing the expression vector according to the sixth aspect of the present invention, or with the polynucleotide according to the fifth aspect of the present invention integrated into a genome thereof.

In another preferred embodiment, the host cell comprises a prokaryotic cell or an eukaryotic cell.

In another preferred embodiment, the host cell is selected from the group consisting of: a mammalian cell, *E. coli*, a yeast cell, bacteriophage, and a combination thereof.

In another preferred embodiment, the prokaryotic cell is selected from the group consisting of: *Escherichia coli, Bacillus subtilis, Lactobacillus, Streptomyces, Proteus mirabilis*, and a combination thereof.

In another preferred embodiment, the eukaryotic cell is selected from the group consisting of: *Pichia pastoris, Saccharomyces cerevisiae, Schizosaccharomyces pombe, Trichoderma*, and a combination thereof.

In another preferred embodiment, the eukaryotic cell is selected from the group consisting of: an insect cell such as a grass armyworm cell, a plant cell such as a tobacco cell, a BHK cell, a CHO cell, a COS cell, a myeloma cell, and a combination thereof.

In another preferred embodiment, the host cell is preferably a mammalian cell, and more preferably an HEK293 cell, CHO cell, BHK cell, NSO cell, or COS cell.

In an eighth aspect of the present invention, it provides a method for producing an anti-CD47 single domain antibody or an Fc fusion protein thereof, comprising the steps of:

(a) cultivating the host cell according to the seventh aspect of the present invention under conditions suitable for the production of a single-domain antibody and a Fc fusion protein thereof, thereby obtaining a culture containing the anti-CD47 single domain antibody or the Fc fusion protein thereof; and (b) isolating or recovering the anti-CD47 single domain antibody or the Fc fusion protein thereof from the culture.

In another preferred embodiment, the anti-CD47 single domain antibody has an amino acid sequence as shown in SEQ ID NO: 8 or 14 or 16.

In a ninth aspect of the present invention, it provides an immunoconjugate containing:

(a) the VHH chain of the anti-CD47 single domain antibody according to the second aspect of the present invention, or the anti-CD47 single domain antibody according to the third aspect of the present invention, or the anti-CD47 single domain antibody Fc fusion protein according to the fourth aspect of the present invention; and (b) a coupling moiety selected from the group consisting of: a detectable marker, drug, toxin, cytokine, radionuclide, and enzyme.

In another preferred embodiment, the coupling moiety is a drug or toxin.

In another preferred embodiment, the coupling moiety is a detectable marker.

In another preferred embodiment, the conjugate is selected from: a fluorescent or luminescent marker, radioactive marker, MRI (magnetic resonance imaging) or CT (electronic computer X-ray tomography) contrast agent, or enzyme capable of producing a detectable product, radionuclide, biotoxin, cytokine (such as IL-2, etc.), antibody, antibody Fc fragment, antibody scFv fragment, gold nanoparticle/nanorod, virus particle, liposome, nanomagnetic particle, prodrug activating enzyme (e.g., DT-diaphorase (DTD) or biphenyl hydrolase-like protein (BPHL)), chemotherapeutic agent (e.g., cisplatin), or nanoparticle in any form, etc.

In another preferred embodiment, the immunoconjugate contains: a multivalent (e.g., bivalent) VHH chain of the anti-CD47 single domain antibody according to the second aspect of the present invention, the anti-CD47 single domain antibody according to the third aspect of the present invention, or the anti-CD47 single domain antibody Fc fusion protein according to the fourth aspect of the present invention.

In another preferred embodiment, the multivalent means that the amino acid sequence of the immunoconjugate contains multiple repeats of the VHH chain of the anti-CD47 single domain antibody according to the second aspect of the present invention, the anti-CD47 single domain antibody according to the third aspect of the present invention, or the anti-CD47 single domain antibody Fc fusion protein according to the fourth aspect of the present invention.

In a tenth aspect of the present invention, it provides a use of the anti-CD47 single domain antibody according to the third aspect of the present invention and the anti-CD47 single domain antibody Fc fusion protein according to the fourth aspect for preparing (a) a reagent for the detection of CD47 molecule; (b) a medicine for the treatment of a tumor.

In another preferred embodiment, the detection includes flow cytometry detection and cellular immunofluorescence detection.

In an eleventh aspect of the present invention, it provides a pharmaceutical composition comprising:

(i) the complementarity determining region CDR of the anti-CD47 single domain antibody VHH chain according to the first aspect of the present invention, the VHH chain of the anti-CD47 single domain antibody according to the second aspect of the present invention, the anti-CD47 single domain antibody according to the third aspect of the present invention, the anti-CD47 single domain antibody Fc fusion protein according to the fourth aspect of the present invention or the immunoconjugate according to the ninth aspect of the present invention; and (ii) a pharmaceutically acceptable carrier.

In another preferred embodiment, the pharmaceutical composition is in the form of an injection.

In another preferred embodiment, the pharmaceutical composition is used for preparing a medicine for treating a tumor, and the tumor is selected from the group consisting of: gastric cancer, liver cancer, leukemia, renal carcinoma, lung cancer, carcinoma of small intestine, bone cancer, prostate carcinoma, colorectal cancer, breast cancer, colon cancer, prostate carcinoma, cervical cancer, lymphoma, adrenal tumor, and bladder tumors.

In a twelfth aspect of the present invention, it provides one or more uses of the anti-CD47 single domain antibody according to the third aspect of the present invention:

(i) for the detection of a human CD47 molecule;
(ii) for the flow cytometry detection;
(iii) for the cellular immunofluorescence detection;
(iv) for the treatment of a tumor;
(v) for the tumor diagnosis.

In another preferred embodiment, the use is diagnostic and/or non-diagnostic, and/or therapeutic and/or non-therapeutic.

In a thirteenth aspect of the present invention, it provides one or more uses of the anti-CD47 single domain antibody Fc fusion protein according to the fourth aspect of the present invention:

(i) for the detection of a human CD47 molecule;
(ii) for the flow cytometry detection;
(iii) for the cellular immunofluorescence detection;
(iv) for the treatment of a tumor;
(v) for the tumor diagnosis.

In another preferred embodiment, the use is diagnostic and or non-diagnostic, and/or therapeutic and/or non-therapeutic.

In a fourteenth aspect of the present invention, it provides a recombinant protein, which has:

(i) the sequence of the heavy chain variable region VHH according to the second aspect of the present invention, or the sequence of the single domain antibody according to the third aspect of the present invention, or the anti-CD47 single domain antibody Fc fusion protein according to the fourth aspect of the present invention; and (ii) an optional tag sequence to aid expression and/or purification.

In another preferred embodiment, the tag sequence includes a 6His tag, an HA tag, or an Fc tag.

In another preferred embodiment, the recombinant protein specifically binds to CD47 protein.

In a fifteenth aspect of the present invention, it provides a use of the VHH chain according to the second aspect of the present invention, the single domain antibody according to the third aspect of the present invention, the anti-CD47 single domain antibody Fc fusion protein according to the fourth aspect, or the immunoconjugate according to the ninth aspect of the present invention for the preparation of the medicament, reagent, detection plate or kit;

wherein the reagent, detection plate or kit is used for: detecting CD47 protein in the sample;

wherein the medicament is used for treating or preventing a tumor expressing CD47 (i.e., CD47 positive) protein.

In another preferred embodiment, the tumor includes: lymphoma, ovarian cancer, leukemia, melanoma, gastric cancer, lymphoma, liver cancer, leukemia, renal carcinoma, lung cancer, carcinoma of small intestine, bone cancer, prostate carcinoma, colorectal cancer, breast cancer, colon cancer, prostate carcinoma, or adrenal tumor.

In a sixteenth aspect of the present invention, it provides a method for detecting CD47 protein in a sample, which comprises the steps of:

(1) contacting the sample with the single domain antibody according to the third aspect of the present invention or the anti-CD47 single domain antibody Fc fusion protein according to the fourth aspect;

(2) detecting whether an antigen-antibody complex is formed, wherein the formation of the complex indicates the presence of CD47 protein in the sample.

In another preferred embodiment, the method is a non-diagnostic and non-therapeutic method.

In a seventeenth aspect of the present invention, it provides a method of treating a disease, comprising administering to a subject in need the single domain antibody according to the third aspect of the present invention, or the anti-CD47 single domain antibody Fc according to the fourth aspect or the immunoconjugate according to the ninth aspect of the present invention.

In another preferred embodiment, the subject includes a mammal, such as human.

In an eighteenth aspect of the present invention, it provides a framework region FR of an anti-CD47 single domain antibody VHH chain, wherein the framework region FR of the VHH chain is composed of FR1 as shown in SEQ ID NO: 1, FR2 as shown in SEQ ID NO: 2, FR3 as shown in SEQ ID NO: 3, and FR4 as shown in SEQ ID NO: 4.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figure 1:
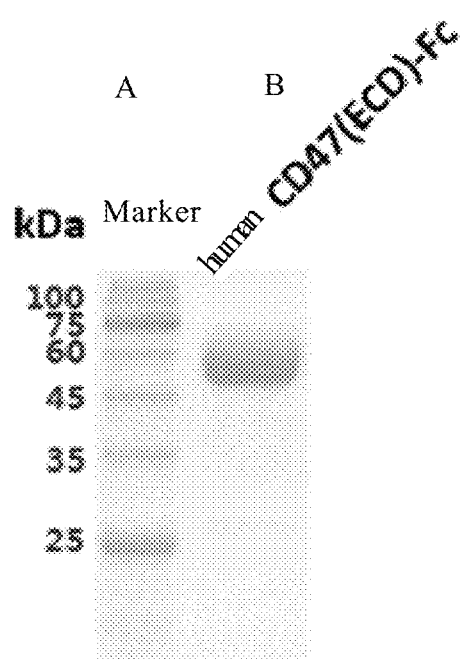
FIG. 1 is a SDS-PAGE diagram of an antigen protein and single-domain antibody purification. In the figure, A is for a nucleic acid molecule standard, and B is for a purified hCD47 (ECD)-Fc protein, wherein the protein is expressed by an HEK293F cell with a purity of more than 90%.

Through the extensive and intensive research and a lot of screening, the present inventor has successfully obtained a class of anti-CD47 single domain antibodies. The experimental results show that the CD47 single domain antibodies obtained by the present invention can effectively bind to CD47.

Specifically, the present invention utilizes human-derived CD47 antigen protein to immunize camels to obtain a high-quality immune single domain antibody gene library, and then the CD47 protein molecule is coupled to the ELISA Plate to display the correct spatial structure of the CD47 protein. In this form of antigen, the phage display technology is used to screen the immune single domain antibody gene library (camel heavy chain antibody phage display gene library) to obtain the CD47 specific single domain antibody gene. This gene is then transferred to E. coli to obtain a single domain antibody strain that can be efficiently expressed in E. coli and has high specificity.

As used herein, the terms "single domain antibody of the present invention", "anti-CD47 single domain antibody of the present invention", and "CD47 single domain antibody of the present invention" can be used interchangeably and refer to single domain antibodies that specifically recognize and bind to CD47 (including human CD47). Particularly preferred is a single domain antibody whose amino acid sequence of the VHH chain is shown in SEQ ID NO: 8 or 14.

As used herein, the term "antibody" or "immunoglobulin" is a heterotetrameric glycoprotein of about 150,000 Daltons with the same structural characteristics, which consists of two identical light chains (L) and two identical heavy chains (H). Each light chain is connected to the heavy chain through a covalent disulfide bond, and the number of disulfide bonds between heavy chains of different immunoglobulin isotypes is different. Each heavy and light chain also has regularly spaced disulfide bonds in the chain. Each heavy chain has a variable region (VH) at one end, followed by multiple constant regions. Each light chain has a variable region (VL) at one end and a constant region at the other end. The constant region of the light chain is opposite to the first constant region of the heavy chain, and the variable region of the light chain is opposite to the variable region of the heavy chain. Special amino acid residues form an interface between the variable regions of the light chain and the heavy chain.

As used herein, the terms "single domain antibody (VHH)", "single domain antibody" (single domain antibody, sdAb, or nanobody) have the same meaning, and refer to the cloning of the variable region of an antibody heavy chain and the construction of a single domain antibody (VHH) consisting of only one heavy chain variable region, which is the smallest antigen-binding fragment with complete functions. Usually, the antibody that naturally lacks the light chain and the heavy chain constant region 1 (CH1) is obtained, and then the variable region of the antibody heavy chain is cloned to construct a single domain antibody (VHH) consisting of only one heavy chain variable region.

As used herein, the term "variable" means that certain parts of the variable region in an antibody differ in sequence, which forms the binding and specificity of various specific antibodies for their specific antigens. However, the variability is not evenly distributed throughout the variable region of the antibody. It is concentrated in three segments called complementarity determining regions (CDRs) or hypervariable regions in the light chain variable regions and heavy chain variable regions. The more conserved part of the variable region is called the framework region (FR). The variable regions in the natural heavy and light chains each contain four FR regions, which are roughly in the β-fold configuration, connected by the three CDRs that form the connecting loop, and in some cases part of the β-folded structure may be formed. The CDRs in each chain are closely together through the FR region and together with the CDRs of the other chain to form the antigen-binding site of the antibody (see Kabat et al., NIH Publ. No. 91-3242, Volume I, pages 647-669) (1991)). The constant regions are not directly involved in the binding of antibodies to antigens, but they exhibit different effector functions, such as antibody-dependent cytotoxicity involved in antibodies.

As known to those skilled in the art, immunoconjugates and fusion expression products include: conjugates formed by combining drugs, toxins, cytokines, radionuclides, enzymes, and other diagnostic or therapeutic molecules with the antibodies or fragments thereof of the present invention. The present invention also includes cell surface markers or antigens that bind to the anti-CD47 protein antibody or fragments thereof.

As used herein, the terms "heavy chain variable region" and "VH" can be used interchangeably.

As used herein, the terms "variable region" and "complementarity determining region (CDR)" can be used interchangeably.

In a preferred embodiment of the present invention, the heavy chain variable region of the antibody includes three complementarity determining regions CDR1, CDR2, and CDR3.

In a preferred embodiment of the present invention, the heavy chain of the antibody includes the above heavy chain variable region and heavy chain constant region.

In the present invention, the terms "antibody of the present invention", "protein of the present invention", or "polypeptide of the present invention" can be used interchangeably, and refer to a polypeptide that specifically binds to the CD47 protein, such as a protein or polypeptide having a heavy chain variable region. They may or may not contain a starting methionine.

The present invention also provides other proteins or fusion expression products comprising the antibodies of the present invention. Specifically, the present invention includes any protein or protein conjugate and fusion expression product having a heavy chain containing a variable region (i.e., immunoconjugate and fusion expression product), as long as the variable region is the same as the heavy chain variable region of the antibody of the present invention or has at least 90% homology with that, preferably at least 95% homology with that.

In general, the antigen-binding properties of antibodies can be described by three specific regions located in the variable region of the heavy chain, called variable regions (CDR). The segment is divided into 4 framework regions (FR), the amino acid sequences of the 4 FRs are relatively conservative, and do not directly participate in the binding reaction. These CDRs form a circular structure, and the β-pleated sheet formed by the FRs in between are close to each other in space structure. The CDRs on the heavy chain and the CDRs on the corresponding light chain constitute the antigen binding site of the antibody. The amino acid sequences of antibodies of the same type can be compared to determine which amino acids constitute the FR or CDR regions.

The variable regions of the heavy chains of the antibodies of the present invention are of particular interest because at least part of them are involved in binding antigens. Therefore, the present invention includes those molecules having a CDR-containing antibody heavy chain variable region, as long as their CDRs have more than 90% (preferably more than 95%, most preferably more than 98%) homology with the CDRs identified herein.

The present invention includes not only whole antibodies, but also fragments of antibodies with immunological activity or fusion proteins formed by antibodies and other sequences. Therefore, the present invention also includes fragments, derivatives and analogs of the antibodies.

As used herein, the terms "fragment", "derivative" and "analog" refer to a polypeptide that substantially retains the same biological function or activity of the antibody of the present invention. The polypeptide fragment, derivative or analog of the present invention may be (i) a polypeptide having one or more conservative or non-conservative amino acid residues (preferably conservative amino acid residues) substituted, and such substituted amino acid residues may or may not be encoded by the genetic code, or (ii) a polypeptide with a substitution group in one or more amino acid residues, or (iii) a polypeptide formed by the fusion of a mature polypeptide with another compound (such as a compound that extends the half-life of the polypeptide, such as polyethylene glycol), or (iv) a polypeptide formed by fusing the additional amino acid sequence to the polypeptide sequence (such as a leader sequence or secretion sequence or a sequence or proprotein sequence used to purify the polypeptide, or a fusion protein formed with a 6His tag). According to the teachings herein, these fragments, derivatives and analogs are within the scope of those skilled in the art.

The antibody of the present invention refers to a polypeptide having CD47 protein binding activity and containing the above-mentioned CDR regions. The term also includes variant forms of polypeptides containing the above CDR regions that have the same function as the antibodies of the present invention. These variant forms include (but are not limited to): one or more (usually 1-50, preferably 1-30, more preferably 1-20, most preferably 1-10) amino acid deletions, insertions and/or substitutions, and one or several (usually within 20, preferably within 10, and more preferably within 5) amino acids addition to the C-terminal and/or N-terminal. For example, in the art, the substitution of amino acids with close or similar properties usually does not change the function of the protein. As another example, adding one or several amino acids to the C-terminus and/or N-terminus usually does not change the function of the protein. The term also includes active fragments and active derivatives of the antibodies of the present invention.

The variant forms of the polypeptide include: homologous sequences, conservative variants, allelic variants, natural mutants, induced mutants, proteins encoded by DNA that can hybridize with DNA encoding the antibody of the present invention under highly or lowly stringent conditions, and polypeptides or proteins obtained using antiserum against antibodies of the present invention.

The present invention also provides other polypeptides, such as fusion proteins comprising single domain antibodies or fragments thereof. In addition to almost full-length polypeptides, the present invention also includes fragments of single domain antibodies of the present invention. Generally, the fragment has at least about 50 consecutive amino acids, preferably at least about 50 consecutive amino acids, more preferably at least about 80 consecutive amino acids, and most preferably at least about 100 consecutive amino acids of the antibody of the present invention.

In the present invention, "conservative variant of the antibody of the present invention" refers to that based on the amino acid sequence of the antibody of the present invention, at most 10, preferably at most 8, more preferably at most 5, and most preferably at most 3 amino acids are replaced by amino acids with similar or close properties to form a polypeptide.

The present invention also provides polynucleotide molecules encoding the above antibodies or fragments or fusion proteins thereof. The polynucleotide of the present invention may be in the form of DNA or RNA. DNA forms include cDNA, genomic DNA, or synthetic DNA. DNA can be single-stranded or double-stranded. DNA can be a coding strand or a non-coding strand.

The polynucleotide encoding the mature polypeptide of the present invention includes: a coding sequence encoding only the mature polypeptide; a coding sequence encoding the mature polypeptide with various additional coding sequences; a coding sequence encoding the mature polypeptide (and optional additional coding sequences) with a non-coding sequence.

The term "polynucleotide encoding a polypeptide" may include a polynucleotide encoding the polypeptide, or a polynucleotide further containing additional coding and/or non-coding sequences.

The present invention also relates to polynucleotides that hybridize to the above-mentioned sequences and have at least 50%, preferably at least 70%, and more preferably at least 80% identity between the two sequences. The present invention particularly relates to polynucleotides that can hybridize to the polynucleotides of the present invention under stringent conditions. In the present invention, "stringent conditions" means: (1) hybridization and elution at lower ionic strength and higher temperature, such as 0.2× SSC, 0.1% SDS, 60° C.; or (2) denaturing agent, such as 50% (v/v) formamide, 0.1% calf serum/0.1% Ficoll, 42° C., etc. is added during hybridization; or (3) hybridization occurs only when the identity between the two sequences is at least 90%, and more preferably at least 95%. Furthermore, the polypeptide encoded by the hybridizable polynucleotide has the same biological function and activity as the mature polypeptide.

The full-length nucleotide sequence of the antibody of the present invention or a fragment thereof can generally be obtained by PCR amplification method, recombination method or artificial synthesis method. A feasible method is to use synthetic methods to synthesize the relevant sequences, especially when the fragment length is short. Generally, a fragment with a very long sequence can be obtained by synthesizing multiple small fragments and then connecting them. In addition, the coding sequence of the heavy chain and the expression tag (such as 6His) can also be fused together to form a fusion protein.

Once the relevant sequence is obtained, the relevant sequence can be obtained in large quantities by the recombination method. This is usually done by cloning it into a vector, then transferring it into a cell, and then isolating the relevant sequence from the propagated host cell by conventional methods. The biomolecules (nucleic acids, proteins, etc.) involved in the present invention include biomolecules that exist in an isolated form.

At present, the DNA sequence encoding the protein (or a fragment or a derivative thereof) of the present invention can be obtained completely by chemical synthesis. This DNA sequence can then be introduced into various existing DNA molecules (or vectors) and cells known in the art. In addition, mutations can also be introduced into the protein sequence of the present invention by chemical synthesis.

The present invention also relates to vectors containing the appropriate DNA sequence as described above and an appropriate promoter or control sequence. These vectors can be used to transform appropriate host cells so that they can express proteins.

The host cell may be a prokaryotic cell, such as a bacterial cell; or a lower eukaryotic cell, such as a yeast cell; or a higher eukaryotic cell, such as a mammalian cell. Representative examples are: *Escherichia coli, Streptomyces*; bacterial cells of *Salmonella typhimurium*; fungal cells such as yeast; insect cells of *Drosophila* S2 or Sf9; animal cells of CHO, COS7, 293 cells, etc.

Transformation of host cells with recombinant DNA can be performed using conventional techniques well known to those skilled in the art. When the host is a prokaryotic organism such as *E. coli*, competent cells that can absorb DNA can be harvested after the exponential growth phase and treated with the CaCl2 method. The procedures used are well known in the art. Another method is to use MgCl2. If necessary, transformation can also be carried out by electroporation. When the host is a eukaryote, the following DNA transfection methods can be used: calcium phosphate co-precipitation method, conventional mechanical methods such as microinjection, electroporation, liposome packaging, etc.

The obtained transformant can be cultured by a conventional method to express the polypeptide encoded by the gene of the present invention. Depending on the host cell used, the medium used in the culture can be selected from various conventional mediums. The cultivation is carried out under conditions suitable for the growth of host cells. When the host cell grows to an appropriate cell density, the selected promoter is induced by an appropriate method (such as temperature conversion or chemical induction), and the cell is cultured for a period of time.

The recombinant polypeptide in the above method may be expressed in a cell or on a cell membrane, or secreted out of the cell. If necessary, the recombinant protein can be isolated and purified by various separation methods using its physical, chemical and other characteristics. These methods are well known to those skilled in the art. Examples of these methods include, but are not limited to: conventional renaturation treatment, treatment with protein precipitation agent (salting out method), centrifugation, disruption of bacteria through penetration, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

The antibody of the present invention may be used alone, or may be combined or coupled with a detectable marker (for diagnostic purposes), a therapeutic agent, a PK (protein kinase) modified portion, or a combination of any of these.

Detectable markers for diagnostic purposes include, but are not limited to: fluorescent or luminescent markers, radioactive markers, MRI (magnetic resonance imaging) or CT (electronic computer X-ray tomography) contrast agents, or an enzyme capable of producing a detectable product.

Therapeutic agents that can be combined or conjugated with the antibodies of the present invention include, but are not limited to: 1. radionuclides; 2. biotoxin; 3. cytokines such as IL-2, etc.; 4. gold nanoparticles/nanorods; 5. viruses particles; 6. liposomes; 7. magnetic nanosphere; 8. drug-activating enzymes (e.g., DT-diaphorase (DTD) or biphenylhydrolase-like protein (BPHL)); 9. chemotherapeutic agents (e.g., cis-platinum) or any form of nanoparticles, etc.

Integrin-Related Protein CD47

Integrin-related protein (CD47) is a 50 kD membrane glycoprotein that belongs to the members of immunoglobulin superfamily. Because it is first isolated from leukocytes and placenta together with integrin αVβ3 in the form of membrane surface protein, and its function is mostly related to integrin, so that it is called integrin-associated protein (IAP). CD47 is widely expressed on the surface of hematopoietic cells (erythrocyte, lymphocytes, platelets, monocytes, and neutrophils) as well as in placenta, liver, and brain tissue. Through the interaction with its ligands, it participates in various physiological activities of the organism, such as the activation and clearance of platelet, chemotaxis and phagocytosis of macrophages, hematopoiesis supported by stromal cells, and migration and activation process of neutrophils. CD47 and inhibitory receptor signal-regulating protein a are mutually receptors and ligands, which can form the CD47-SIRPa signaling complex, which has the role of mediating bidirectional signal regulation and regulating various immune response processes. As a self-marker of erythrocyte, it inhibits the removal of erythrocyte and participates in the pathogenesis of hemolytic anemia. On normal hematopoietic stem cells (HSCs), the significance of CD47 expression is to maintain its relative stability in the body. In malignant tumors such as leukemia, non-Hodgkin's lymphoma, bladder cancer, and breast cancer, CD47 is highly expressed on the surface of tumor cells, suggesting a poor clinical prognosis. By taking this "don't eat me" signal, tumor cells escape tumor immunity.

Pharmaceutical Composition

The present invention also provides a composition. Preferably, the composition is a pharmaceutical composition, which contains the above antibody or an active fragment or fusion protein thereof, and a pharmaceutically acceptable carrier. Generally, these substances can be formulated in a non-toxic, inert and pharmaceutically acceptable aqueous carrier medium, wherein the pH is usually about 5-8, preferably about 6-8, although the pH can vary depending on the nature of the substance being formulated and the condition to be treated. The formulated pharmaceutical composition can be administered by conventional routes, including (but not limited to): intratumoral, intraperitoneal, intravenous, or topical administration.

The pharmaceutical composition of the present invention can be directly used to bind CD47 protein molecules, and thus can be used to treat tumors. In addition, other therapeutic agents can be used simultaneously.

The pharmaceutical composition of the present invention contains a safe and effective amount (such as 0.001-99 wt %, preferably 0.01-90 wt %, more preferably 0.1-80 wt %) of the above single domain antibody (or its conjugate) of the present invention and a pharmaceutical acceptable carrier or excipient. Such carriers include (but are not limited to): saline, buffer, glucose, water, glycerin, ethanol, and a combination thereof. The pharmaceutical preparation should match the mode of administration. The pharmaceutical composition of the present invention can be prepared in the form of an injection, for example, prepared by a conventional method using a physiological saline or an aqueous solution containing glucose and other adjuvants. Pharmaceutical compositions such as injections and solutions are preferably manufactured under sterile conditions. The amount of active ingredient administered is a therapeutically effective amount, for example, about 10 micrograms/kg body weight to about 50 mg/kg body weight per day. In addition, the polypeptide of the present invention can be used together with other therapeutic agents.

When using a pharmaceutical composition, a safe and effective amount of an immunoconjugate is administered to a mammal, wherein the safe and effective amount is usually at least about 10 μg/kg body weight, and in most cases does not exceed about 50 mg/kg body weight, preferably the dose is about from 10 micrograms/kg body weight to about 10 mg/kg body weight. Of course, the specific dosage should also consider factors such as the route of administration, the patient's health status, etc., which are within the skills of skilled physicians.

Labeled Single Domain Antibody

In a preferred embodiment of the present invention, the single domain antibody carries a detectable label. More preferably, the label is selected from the group consisting of: isotopes, colloidal gold labels, colored labels or fluorescent labels.

Colloidal gold labeling can be performed using methods known to those skilled in the art. In a preferred embodiment of the present invention, the anti-CD47 single domain antibody is labeled with colloidal gold to obtain a colloidal gold labeled single domain antibody.

The anti-CD47 single domain antibody of the present invention has good specificity and high titer.

Detection Method

The present invention also relates to a method for detecting CD47 protein. The method steps are roughly as follows: obtaining a cell and/or tissue sample; dissolving the sample in a medium; and detecting the level of CD47 protein in the dissolved sample.

In the detection method of the present invention, the sample used is not particularly limited, and a representative example is a cell-containing sample present in a cell preservation solution.

Kit

The present invention also provides a kit containing the antibody (or a fragment thereof) or a detection plate of the present invention. In a preferred embodiment of the present invention, the kit further includes a container, an instruction for use, a buffer, and the like.

The present invention also provides a detection kit for detecting the level of CD47, which includes an antibody that recognizes the CD47 protein, a lysis medium for dissolving the sample, general reagents and buffers required for the detection, such as various buffers, detection markers, detection substrates, etc. The detection kit may be an in vitro diagnostic device.

Application

As described above, the single domain antibody of the present invention has a wide range of biological application value and clinical application value, and its application involves the diagnosis and treatment of CD47-related diseases, basic medical research, biological research and other fields. A preferred application is for clinical diagnosis and targeted therapy for CD47.

The main advantages of the present invention include:

(a) The single domain antibody of the present invention is highly specific against human CD47 protein with correct spatial structure.

(b) The single domain antibody of the present invention has good binding activity, blocking activity and affinity, and the humanized antibody has excellent species specificity.

(c) The single domain antibody of the present invention can effectively enhance the phagocytosis of tumor cells by macrophages, and exhibits significant antitumor activity in both human lymphoma model and human ovarian cancer model.

(d) The single domain antibody of the present invention not only does not cause human erythrocyte agglutination in vitro, but also exhibits excellent safety in cynomolgus monkeys.

(e) The production of the single domain antibody of the present invention is simple and has good stability.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (New York: Cold Spring Harbor Laboratory Press, 1989) or as instructed by the manufacturer. Unless otherwise specified, all percentages or parts are by weight.

Example 1: Expression and Purification of Human CD47 Protein (1) Synthesizing the nucleotide sequence of human CD47 on the pCDNA3.1 (-) vector, and then subcloning its extracellular sequence into the pFUSE-IgG1 vector; (2) Extracting the constructed pFUSE-IgG1-hCD47 (ECD) plasmids with the Omega plasmid extraction kit; (3) Cultivating HEK293F cells to an OD of $2.0 \times 10^6$ cells/mL; (4) Mixing the plasmid with transfection reagent PEI at a ratio of 1:3 well and placing it for 20 min, then adding it into HEK293F cells, incubating it at 37° C. in a 6% $CO_2$ shaker incubator for 5-6 days; (5) Collecting the cell supernatant and combine it with Protein A beads for 1 h at room temperature; (6) After washing the beads with phosphate buffer pH 7.0, eluting the protein with 0.1 M pH 3.0 Glycine; (7) Ultrafiltering the eluted protein into PBS, sampling for SDS-PAGE detection after measuring the yield (detection results as shown in FIG. 1), and storing the remaining protein in the refrigerator at −80° C.;

Example 2: Construction and Screening of CD47 Single Domain Antibody Library

Figure 2:
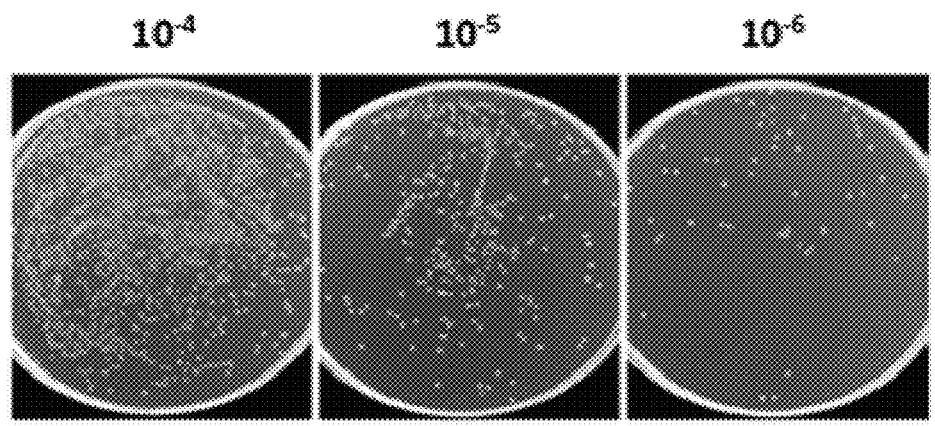
FIG. 2 is the library capacity detection chart of the constructed library, wherein the constructed library is plated after gradient dilution. The figure shows the number of clones with a ⅕ gradient dilution of $10^4$-fold, $10^5$-fold, and $10^6$-fold, and the size of the library is determined by calculating the number of monoclonals, and the library capacity of the library is calculated to be $2.5 \times 10^9$ CFU.
Figure 3:
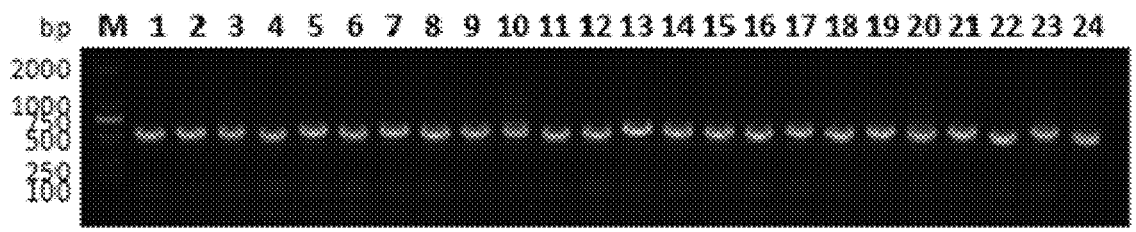
FIG. 3 is a graph of the detection of the insertion rate of the constructed library, showing the results of the detection of the insertion rate of the constructed single domain antibody library. The DNA bands from the left to the right of the gel well are as follows: the first lane is for the DNA molecular marker, and the remaining wells are for the PCR products for detection of the inserts. The PCR product band is about 500 bp; and after testing, the insertion rate of the library reaches 100%.

Library construction: Briefly, (1) mixing 1 mg of hCD47 (ECD)-Fc antigen with Freund's adjuvant in equal volumes to immunize a Xinjiang Bactrian camel once a week for a total of 7 times to stimulate B cells to express an antigen specific single domain antibody; (2) After 7 immunizations, extracting 100 mL camel peripheral blood lymphocytes and extracting total RNA; (3) synthesizing cDNA and using nested PCR to amplify VHH; (4) using restriction enzyme of Pst I and Not I for the digestion of 20 μg pMECS phage display vector (supplied by Biovector) and 10 μg VHH and ligating the two fragments; (5) Transforming the ligation product into electrocompetent cells TG1 to construct a CD47 single domain antibody library and determining the storage capacity, the size of which was $2.5 \times 10^9$ CFU (results as shown in FIG. 2). At the same time, 24 clones were randomly selected for colony PCR detection. The results show that the insertion rate of the constructed library is 100%. FIG. 3 shows the colony PCR results.

Figure 4:
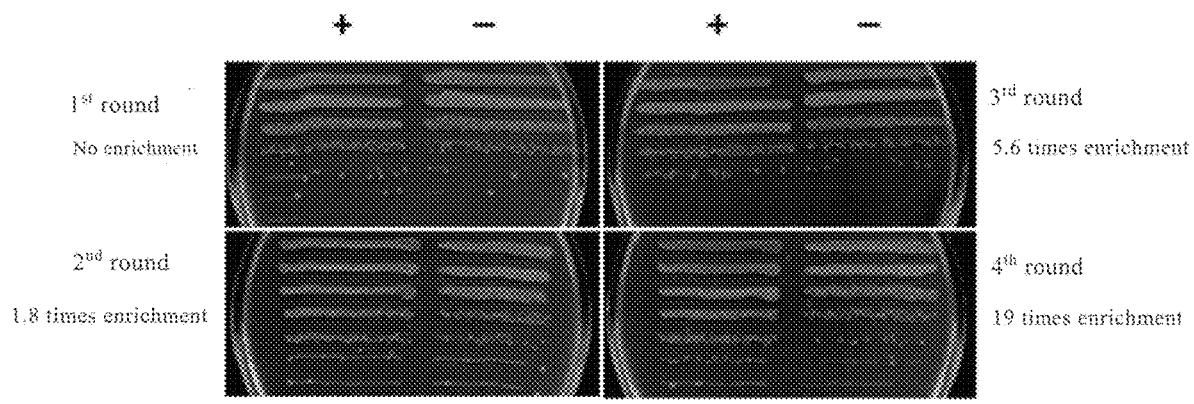
FIG. 4 shows the CD47 single domain antibody screening and enrichment process. There is no enrichment in the library after the first round of panning, 1.8 times enrichment in the second round of panning, 5.6 times enrichment in the third round of panning, and 19 times enrichment in the fourth round of panning.

Antibody screening and identification: Briefly, (1) Coupling 10 μg hCD47 (ECD)-Fc antigen (10 μg Fc in NaHCO3 as a control) dissolved in 100 mM $NaHCO_3$, pH 8.2 on a NUNC ELISA Plate, placing it at 4° C. overnight; (2) adding 100 μL 0.1% BSA the next day and blocking it at room temperature for 2 h; (3) After 2 h, adding 100 μL phage ($2 \times 10^{11}$ CFU immunized camel single domain antibody phage display gene library), at room temperature for 1 h; (4) Washing 5 times with 0.05% PBS+Tween-20 to wash off non-specific phages; (5) Dissociating the phage that specifically binds to CD47 with 100 mM triethanolamine and infecting E. coli TG1 cells growing in logarithmic phase, incubating it at 37° C. for 1 h, generating and purifying phage for the next round of screening, repeating 4 rounds of the same screening process to enrich positive clones (FIG. 4); (6) From the enriched cell culture dishes containing phage, picking 200 single colonies and inoculating them into TB medium containing 100 μg/mL ampicillin (1 L TB medium containing 2.3 g $KH_2PO_4$, 12.52 g $K_2HPO_4$, 12 g peptone, 24 g yeast extract, 4 mL glycerol), after growing to the logarithmic phase, adding IPTG with a final concentration of 1 mM and incubating it overnight at 28° C.; (7) Obtaining a crude antibody by osmosis method and transferring the antibody into the antigen-coated ELISA plate, placing it at room temperature for 1 h; (8) Washing off the unbound antibody with PBST, adding a mouse anti-HA antibody (COVENCE), and placing it at room temperature for 1 h; (9) Washing off unbound antibody with PBST, adding a goat anti-mouse alkaline phosphatase labeled antibody, and placing it at room temperature for 1 h; (10) Washing off unbound antibody with PBST, adding alkaline phosphatase coloring solution, and putting it on the ELISA instrument, and reading the absorption value at 405 nm wavelength; (11) When the OD value of the sample well was more than 3 times the OD value of the control well (Ratio +/−>3), judging it as a positive clone well; (12) shaking the bacteria in the positive clone wells in LB liquid containing 100 μg/mL Amp to extract the plasmid and sequenced.

Figure 5:
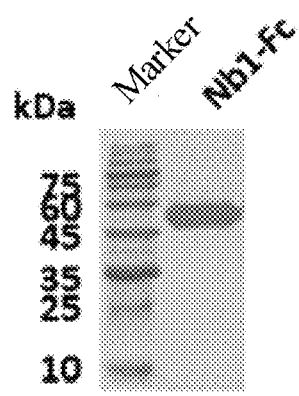
FIG. 5 is a purification diagram of CD47 single domain antibody Fc fusion protein (numbered Nb1-Fc) expressed by a strain of HEK293F system, wherein the single domain antibody corresponds to the amino acid sequence of SEQ ID NO: 8, after purified by Protein A affinity column affinity chromatography, SDS-PAGE electrophoresis of CD47 single domain antibody. The results show that after purification of the CD47 single domain antibody Fc fusion protein Nb1-Fc by this purification process, its purity can reach more than 90%.

Example 3: Expression and Purification of CD47 Single Domain Antibody in Eukaryotic Cell HEK293 and the Detection of the Blocking Function of Single Domain Antibody by Flow Cytometry The expression of the CD47 Nb1-Fc fusion protein in the eukaryotic cell HEK293F: (1) cloning the CD47 Nb1 sequence with correct sequencing results into the pFUSE-IgG4 vector (purchased from Invivogen), and extracting the pFUSE-IgG4-Nb1 plasmid with the Omega plasmid extraction kit; (2) Cultivating HEK293F cells to an OD of $2.0 \times 10^6$ cells/mL; (3) Mixing the plasmid with transfection reagent PEI at a ratio of 1:3 well, placing it for 20 min, and then adding it to HEK293F cells, incubating it at 37° C., 6% $CO_2$ shaker incubator for 5-6 days; (4) Collecting the cell supernatant and combining it with Protein A beads for 1 h at room temperature; (5) Washing the beads with phosphate buffer pH 7.0 and then eluting the protein with 0.1M pH 3.0 Glycine; (6) Ultrafiltration of the eluted protein into PBS, sampling for SDS-PAGE detection after measuring the yield (the detection results were shown in FIG. 5), and storing the remaining protein in the refrigerator at −80° C.

The identification of the blocking function of single domain antibodies by Flow cytometry: Briefly, (1) Preparation of hSIRPa (ECD)-Fc-Biotin, wherein the method of protein biotin refers to the instructions of biotin reagent; (2) Adding $5 \times 10^5$ CD47 stably transferred cells per sample into 0.5% BSA-PBS buffer, adding 5 μg of the above purified CD47 single domain antibody, setting the negative control (hIgG1) and blank group (PBS) in parallel, adding 5 μg of hSIRPa(ECD)-Fc-Biotin to each samples at the same time, incubating at 4° C. for 20 min; (3) washing the cells twice with PBS, adding SA-PE of eBioscience and incubating it at 4° C. for 20 min, washing the cells twice with PBS, and then detecting it by flow cytometry (BD FACS Calibur).

Figure 6:
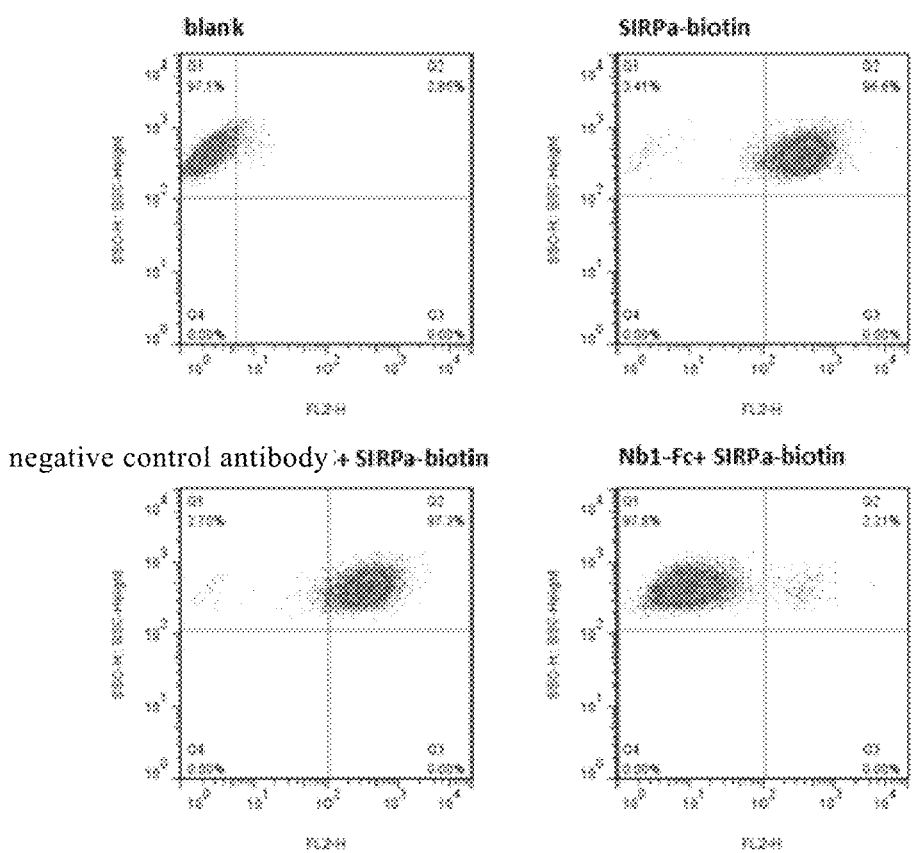
FIG. 6 shows the blocking effect of CD47 single domain antibody Fc fusion protein Nb1-Fc detected by FACS. HEK293T cells stably expressing human full-length CD47 protein are co-reacted with various groups of antibodies and biotinylated hSIRPa (ECD)-Fc protein. It can be seen from the figure that the binding rate of hSIRPa (ECD)-Fc-biotin to stable cells decreases from 97.3% of the negative control group to 2.21%, indicating that the added antibody Nb1-Fc can significantly block the interaction between CD47 and SIRPa. The results show that the Nb1-Fc specific for CD47 of the present invention has a good blocking effect on the binding of CD47 to SIRPa.

The detection results are shown in FIG. 6. The binding rate of hSIRPa (ECD)-Fc-biotin to stably transferred cells was reduced from 97.3% in the negative control group to 2.21%, which indicates that the added single domain antibody Nb1-Fc can significantly block the interaction of CD47 and SIRPa. The results show that the single domain antibody specific for CD47 of the present invention has a good blocking effect on the binding of CD47 to SIRPa.

Example 4: Humanization of CD47 Single Domain Antibody

First, using the CD47 single domain antibody sequence as shown in SEQ ID NO: 8 as a template to search for the homologous structure in the structure database, and the structure in which E value=0.0 and sequence identity ≥70% was used; second, structural comparison on these structures, and according to the crystal structure resolution and the evolutionary tree constructed, finally selecting proteins including 3 dwt for multi-template homology modeling based on the CD47 single domain antibody sequence as shown in SEQ ID NO: 8, and then, according to the ranking of the scoring function, selecting the structure with the lowest molpdf and continuing the following work; and then using the ProtSA server to calculate the solvent accessibility of the residue, that is, the ratio of the residue's folded state to the unfolded solvent accessible area is a criterion, and taking residues greater than 40% as residues exposed to the solvent; finally for the optimal structure of the model, it was sequence compared with DP-47, and replacing the corresponding solvent-exposed residues; Finally, identifying a humanized CD47 single domain antibody (numbered Nb1902), encoded by the amino acid sequence as shown in SEQ ID NO: 14. The antibody sequences before and after humanization correspond to the following Table 1:

| antibody region | sequence numbering (SEQ ID NO.:) | |
| --- | --- | --- |
| | Before humanization | After humanization |
| FR1 | 1 | 10 |
| CDR1 | 5 | 5 |
| FR2 | 2 | 11 |
| CDR2 | 6 | 6 |
| FR3 | 3 | 12 |
| CDR3 | 7 | 7 |
| FR4 | 4 | 13 |
| complete amino acid sequence | 8 | 14 |
| complete nucleotide sequence | 9 | 15 |

Example 5: The Detection of the Blocking Effect of Humanized CD47 Single Domain Antibody Fc Fusion Protein by Flow Cytometry First, the humanized CD47 single-domain antibody Nb1902 sequence (SEQ ID NO: 15) was synthesized on the pFUSE-IgG4PE vector, and the pFUSE-IgG4PE-Nb1902 plasmid was extracted using the Omega plasmid extraction kit. The humanized single domain antibody Nb1902-Fc was expressed using the HEK293F system in the same manner as in Example 3. Subsequently, the two antibodies before and after humanization and the control antibody (B6H12) were diluted to 1 μg/uL, ¼ μg/uL, and ⅛ μg/uL, respectively. It was mixed with ligand of 5 μg hSIRPa (ECD)-Fc-Biotin and mixed with cells stably expressing hCD47. The experimental procedure and detection method were the same as in Example 3. The test results are shown in FIG. 7.

Figure 7:
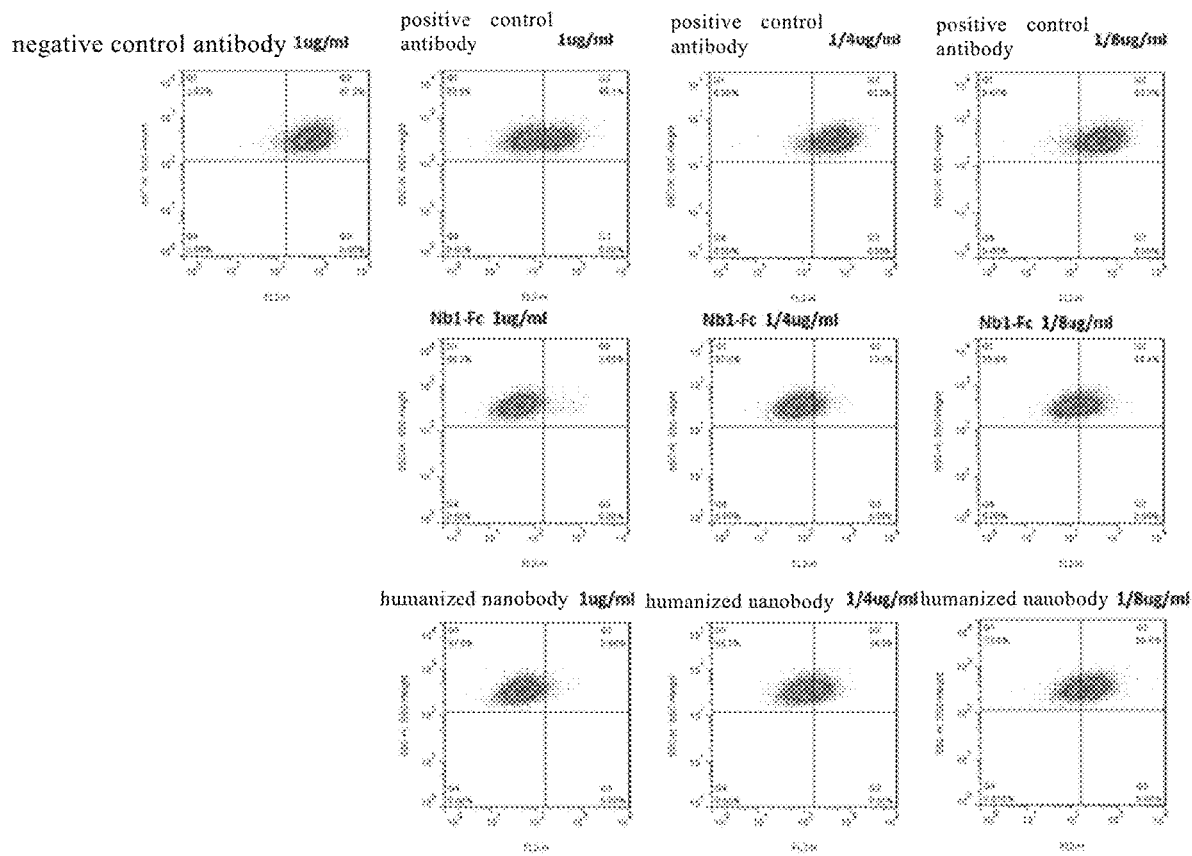
FIG. 7 shows a flow cytometry detection of the blocking effect of humanized CD47 single domain antibody Nb1902-Fc. CD47 protein-expressing stable cells are co-reacted with humanized single domain antibody Nb1902-Fc and biotinylated hSIRPa (ECD)-Fc protein. In the negative control group, the binding rate of hSIRPa (ECD)-Fc-biotin to stable cells is 97.2%, and after adding CD47 single domain antibody and humanized single domain antibody, the binding rate of hSIRPa (ECD)-Fc-biotin to stable cells is significantly reduced, indicating that single domain antibodies before and after humanization can obviously block the interaction between CD47 and hSIRPa.

As can be seen from FIG. 7, the binding rate of hSIRPa (ECD)-Fc-biotin to stably transfected cells in the negative control group is 97.2%. After adding CD47 single domain antibody and humanized single domain antibody, the binding rate of hSIRPa (ECD)-Fc-Biotin to stably transfected cells is significantly reduced, indicating that the single domain antibodies before and after humanization can obviously block the interaction between CD47 and hSIRPa.

Example 6: Detection of $IC_{50}$ of Humanized CD47 Single Domain Antibody Fc Fusion Protein by Flow Cytometry (1) $5 \times 10^5$ CD47 stably transfected cells per sample were added in 0.5% BSA-PBS buffer, gradient diluted CD47 humanized single domain antibody (Nb1902-Fc) and the control antibody B6H12 (the antibody dilution gradient was 30 μg/mL, 25 μg/mL, 20 μg/mL, 15 μg/mL, 10 μg/mL, 5 μg/mL, 3.333 μg/mL, 2.5 μg/mL, 1.667 μg/mL, 1.25 μg/mL, 1 μg/mL, 0.833 μg/mL, 0.625 μg/mL, 0.5 μg/mL, 0.417 μg/mL, 0.313 μg/mL) were added. 100 uL was added in each sample, and a negative control (hIgG4) was set at the same time. 5 μg hSIRPa (ECD)-Fc-Biotin was added to all samples at the same time, and it was incubated for 20 min at 4° C. (2) The cells were washed twice with PBS, SA-PE of eBioscience was added. It was incubated for 20 min at 4° C., and the cells were washed twice with PBS and then detected by flow cytometry (BD FACS Calibur), using graphpad prism 6 software for data processing.

Figure 8:
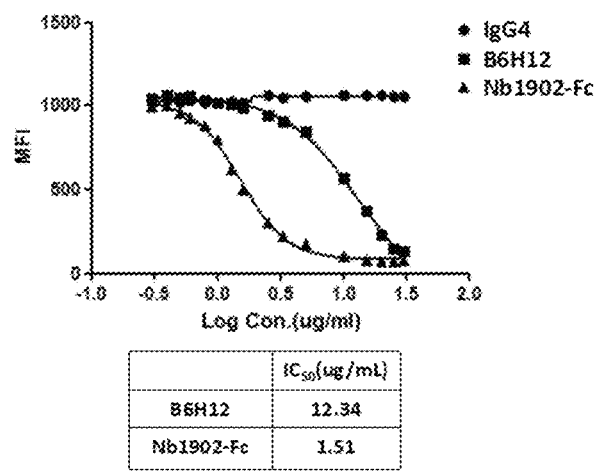
FIG. 8 shows the $IC_{50}$ of humanized single domain antibody Nb1902-Fc and positive control antibody detected by flow cytometry. The results show that the $IC_{50}$ of the humanized CD47 single domain antibody is 1.51 μg/mL, while the $IC_{50}$ of the control antibody B6H12 is 12.34 μg/mL. The blocking effect of the candidate humanized single domain antibody is better than that of the control antibody.

The results are shown in FIG. 8. The $IC_{50}$ of the humanized CD47 single domain antibody is 1.51 μg/mL, while the $IC_{50}$ of the control antibody B6H12 is 12.34 μg/mL. It can be seen that the blocking effect of the candidate humanized single domain antibody is significantly better than that of the control antibody.

Example 7: Affinity Detection of Humanized Single Domain Antibody Fc Fusion Protein (1) The humanized single domain antibody Nb1902-Fc was gradient diluted from 100 nM with PBST, respectively: 100 nM, 66.7 nM, 44.4 nM, 29.6 nM, 19.8 nM, 13.2 nM. The antigen proteins hCD47 (ECD)-Fc and Fc were diluted to 30 μg/mL, respectively. (2) Setting the operating conditions of the instrument: temperature 30° C., shake speed 1000 rpm. Using ProteinA-coated probe (Fortebio Part No: 18-5010) to capture antibody for 180s; binding the gradient diluted antigen for 180s; 300s of dissociation time; 10 mM glycine (PH1.7) regeneration 3 times, 5s for each time. (3) Using ForteBio's Octet System for on-board testing.

Figure 9:
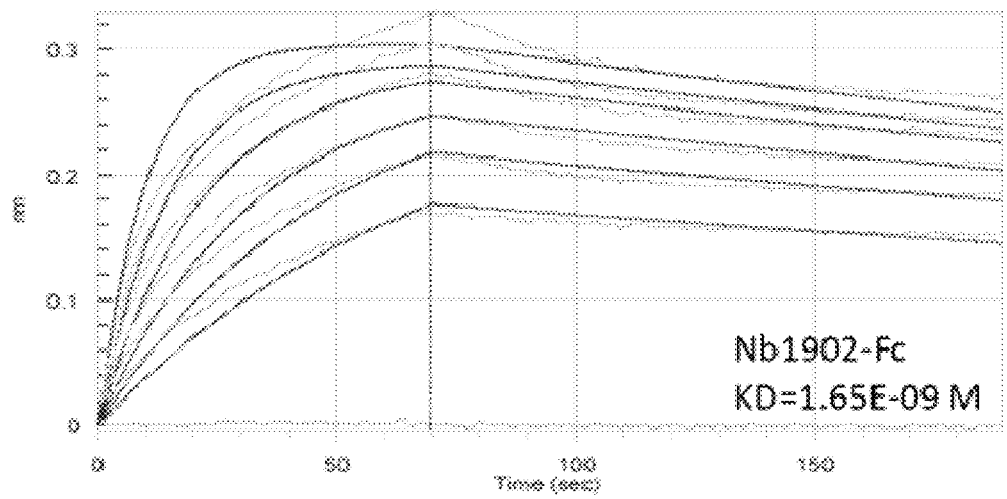
FIG. 9 is the affinity detection result of the humanized single domain antibody Nb1902-Fc. The affinity of humanized antibody Nb1902-Fc is determined to be 1.65E-9 M using ForteBio's Octet System.

The test results are shown in FIG. 9: The affinity of humanized Nb1902-Fc is 1.65E-9 M, which is similar to the reported affinity of the control antibody. Reference: Zeng D, Sun Q et al., Oncotarget. 2016 Dec. 13; 7 (50): 83040-83050.

Example 8: Species Specific Detection of Humanized CD47 Single Domain Antibody (1) The humanized CD47 single domain antibody gene was cloned into *E. coli* expression vector pMECS, and the expression and purification process was the same as in Example 4; (2) Antigen proteins were coated with CD47 (human), CD47 (rat), and CD47 (mouse): 0.5 μg per well (5 μg/mL, 100 μL), coated with IgG4 as a control, overnight at 4° C.; (3) It was washed 3 times with PBST on the next day, and 200 μL of 1% BSA was added to block at room temperature for 2 h; (4) It was washed three times with PBST, and 100 uL of humanized single domain antibody at a concentration of 10 μg/mL was added respectively and reacted at room temperature for 1 h; (5) The unbound antibody was washed off with PBST and mouse anti-HA antibody (COVENCE) was added and placed at room temperature for 1 h; (6) The unbound antibody was washed off with PBST, and the goat anti-mouse alkaline phosphatase-labeled antibody was added and placed at room temperature for 1 h; (7) the unbound antibody was washed off with PBST and the alkaline phosphatase coloring solution was added and the absorption value was read at 405 nm wavelength on an ELISA instrument.

Figure 10:
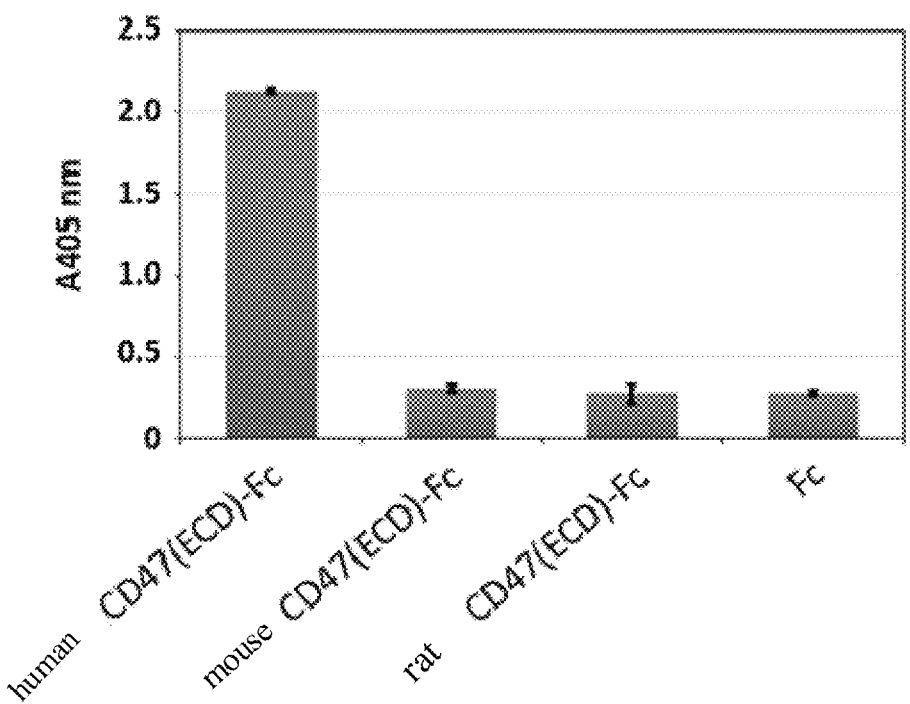
FIG. 10 shows the results of species-specific detection of CD47 single domain antibodies by ELISA. It can be seen that the humanized CD47 single domain antibody Nb1902-Fc only interacts with human-derived CD47, but not with rat and mouse CD47. The candidate humanized single domain antibody has better species specificity.

The specificity of the single domain antibody was determined based on the absorption value. The detection result is shown in FIG. 10: the humanized single domain antibody can interact with human-derived CD47 but not with murine-derived CD47.

Figure 11:
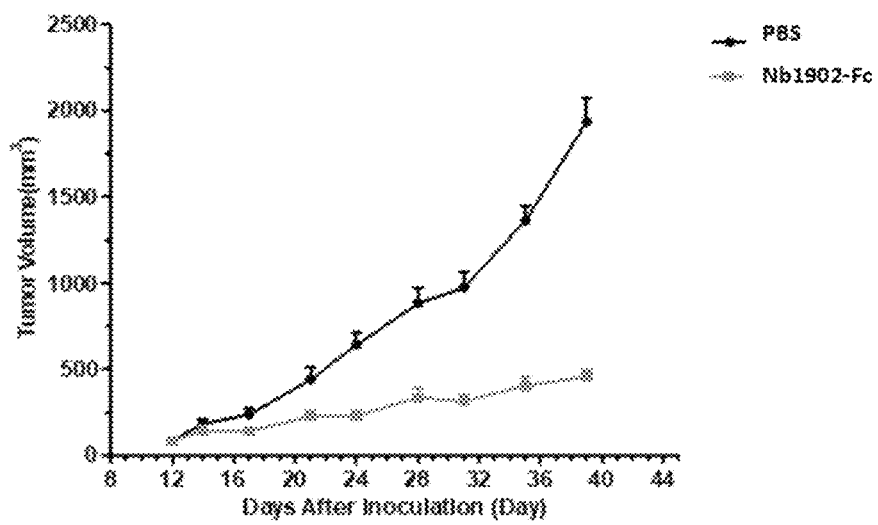
FIG. 11 is the results of the drug efficacy of the humanized CD47 single domain antibody Fc fusion protein in a human lymphoma model. The results show that Nb1902-Fc has a significant tumor suppression effect, and its tumor suppression rate TGI is 80%.

Example 9: The Efficacy of Humanized CD47 Single Domain Antibody Fc Fusion Protein in a Human Lymphoma Model NOG mice were inoculated with Raji cells and divided into two groups for administration after tumor formation (negative group: IgG4; experimental group: Nb1902-Fc). Dosing frequency: once a day for 28 consecutive days. Dosage: 20 mg/kg. The experimental results are shown in FIG. 11: Nb1902-Fc had a significant tumor suppression effect with a tumor suppression rate TGI of 80%.

Figure 12:
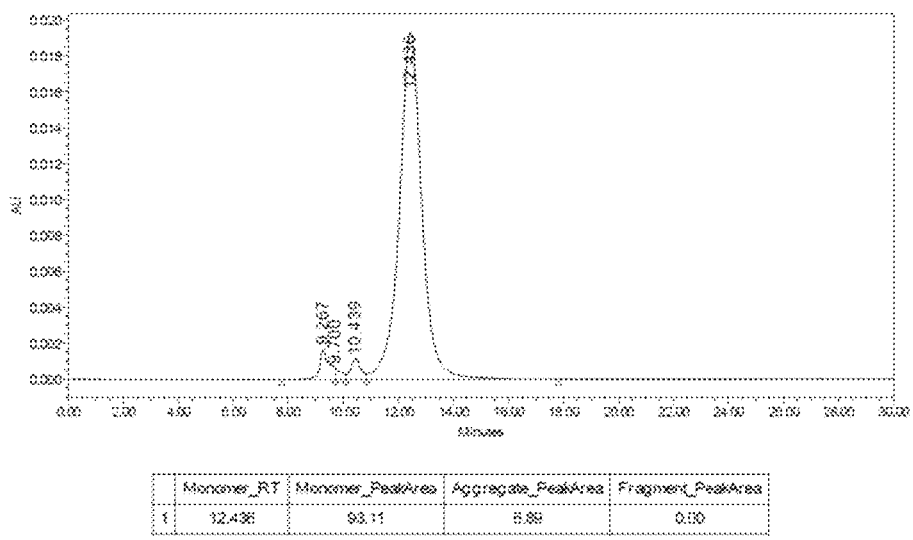
FIG. 12 is a result of the purity of the humanized CD47 antibody Fc fusion protein (MY2238) expressed by the CHO-S system through the SEC-HPLC detection. The results show that the purity of the antibody MY2238 expressed by this system and one-step Protein A affinity purification is 93.11%.
Figure 13A:
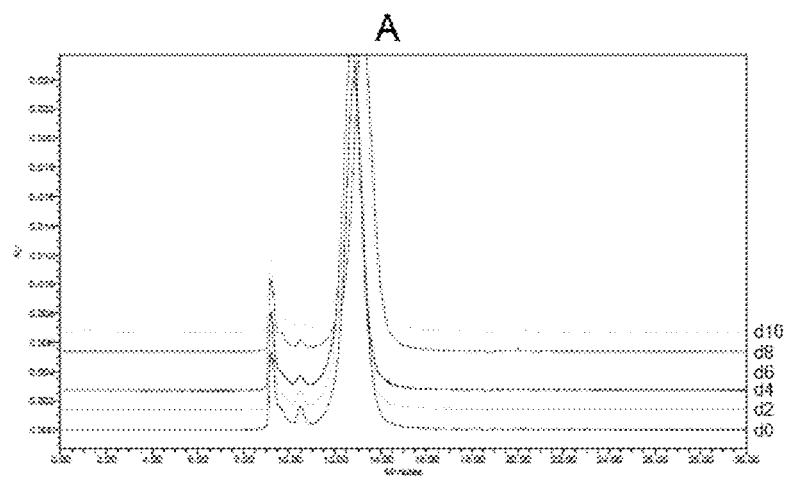
FIGS. 13A-13B shows the stability testing results of humanized CD47 antibody Fc fusion protein. The results show that the antibody shows no obvious aggregation or degradation under the accelerated condition at 25° C. or the severe destruction condition at 40° C., and shows good stability.
Figure 13B:
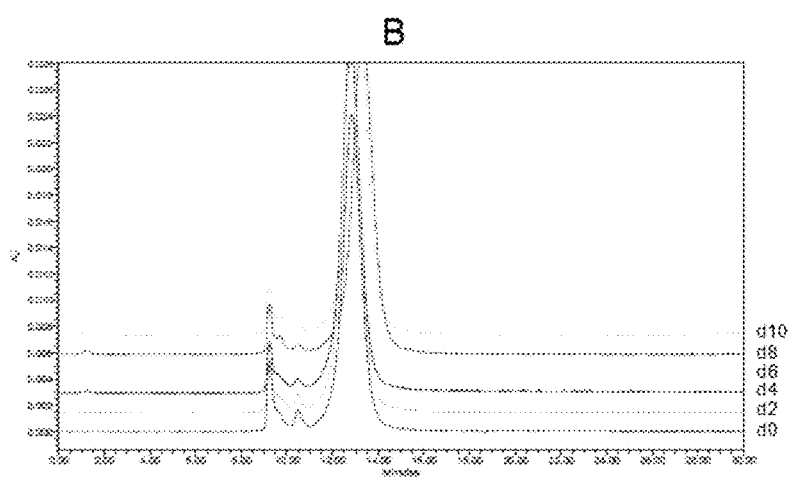
Figure 13C:
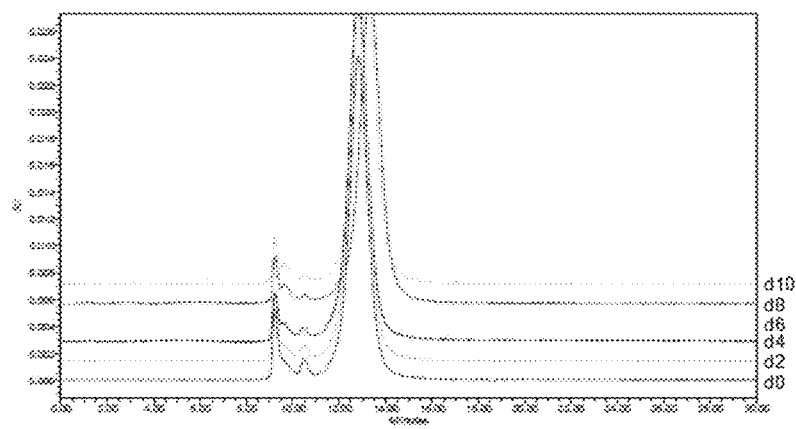
Figure 13D:
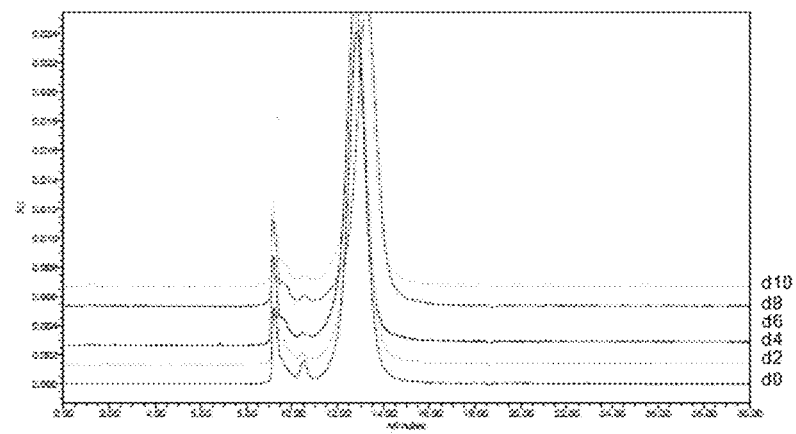
Figure 13E:
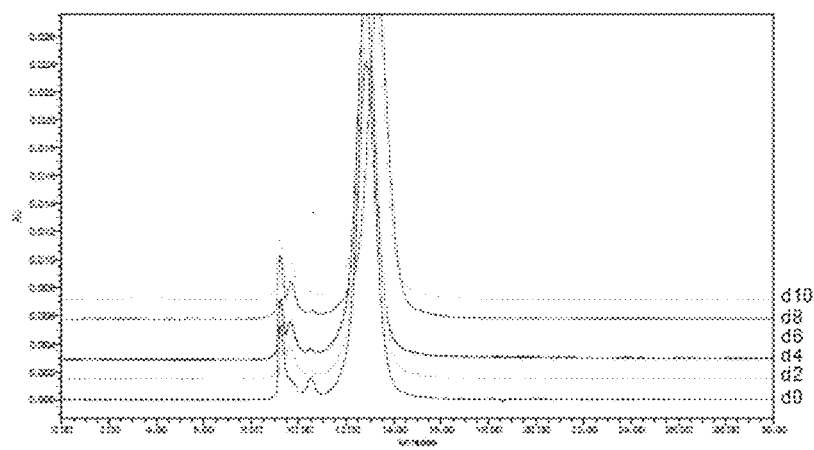
Figure 13F:
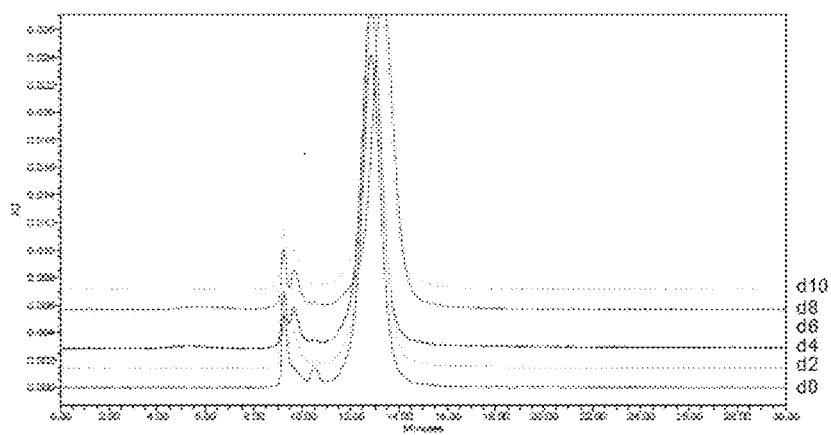

Example 10: Expression of Humanized CD47 Single Domain Antibody in CHO-S System The Nb1902-Fc amino acid sequence was converted into the CHO codon optimized base sequence (as shown in SEQ ID NO: 17), and then the sequence was synthesized into the pCHO1.0 vector. A specific signal peptide was selected for subsequent production and expression of the antibody, and the antibody expressed by this system is numbered MY2238. (1) The OMEGA plasmid extraction kit was used to extract the synthesized plasmid in large quantities and then mixed with PEI and transfected into CHO-S cells. The specific transfection protocol was the same as in Example 1; (2) The protein purification scheme was also the same as in Example 1; (3) The one-step purified sample was analyzed by SEC-HPLC. The results are shown in FIG. 12. After one-step affinity purification, the antibody had a purity of 93.11%, which can be used for subsequent analysis and research.

Example 11: Stability Study of Humanized CD47 Single Domain Antibody Fc Fusion Protein (1) The MY2238 sample was concentrated or diluted to 10 mg/ml; (2) The sample was filtered into a new centrifuge tube with a 0.22 um needle filter; (3) The diluted sample storage solution (1×PBS, pH7.0) was filtered into a new centrifuge tube with a 0.22 um needle filter; (4) 10 mg/mL filtered sample was dispensed into 100 uL per tube and marked according to the corresponding name in the table below;

|  | timing | | | | |
| --- | --- | --- | --- | --- | --- |
| temperature | d2 | d4 | d6 | d8 | d10 |
| 25° C. | T1-10c-d2 | T1-10c-d4 | T1-10c-d6 | T1-10c-d8 | T1-10c-d10 |
| 40° C. | T2-10c-d2 | T2-10c-d4 | T2-10c-d6 | T2-10c-d8 | T2-10c-d10 |

(5) The sample was configured to a final concentration of 5 mg/mL and mixed thoroughly, 100 uL per tube, dispensed and labeled according to the corresponding name of 5 mg/mL in the table below;

| temperature | timing | | | | |
|---|---|---|---|---|---|
| | d2 | d4 | d6 | d8 | d10 |
| 25° C. | T1-5c-d2 | T1-5c-d4 | T1-5c-d6 | T1-5c-d8 | T1-5c-d10 |
| 40° C. | T2-5c-d2 | T2-5c-d4 | T2-5c-d6 | T2-5c-d8 | T2-5c-d10 |

(6) The sample was configured to a final concentration of 1 mg/mL and mixed thoroughly, 100 uL per tube, dispensed and labeled according to the corresponding name in the table below;

| temperature | timing | | | | |
|---|---|---|---|---|---|
| | d2 | d4 | d6 | d8 | d10 |
| 25° C. | T1-1c-d2 | T1-1c-d4 | T1-1c-d6 | T1-1c-d8 | T1-1c-d10 |
| 40° C. | T2-1c-d2 | T2-1c-d4 | T2-1c-d6 | T2-1c-d8 | T2-1c-d10 |

(7) The sample was placed in the corresponding incubator; (8) Sampling and testing at the corresponding detection time point; (9) The sample was diluted to 1 mg/ml with the mobile phase as a testing sample; (10) The testing sample was centrifuged at 10,000 rpm for 3 min, and a pipette was used to transfer the sample supernatant to the sample bottle. It was put into the HPLC auto-sampler, and the sample injection test was performed.

The results are shown in 13A-F. The antibody shows no obvious aggregation or degradation under the accelerated condition of 25° C. or the severe destruction condition of 40° C., and shows good stability.

Example 12: Humanized CD47 Single Domain Antibody Fc Fusion Protein Mediates Phagocytosis of Tumor Cells by Macrophages (1) M1 macrophages were added into a 24-well plate at 1E5/well 5 days in advance; (2) Raji cells were resuspended, transferred to 50 mL centrifuge tube, 3E6 cells were taken after counting; (3) It was centrifuged at 1000 rpm for 5 min, washed once with PBS, resuspended with 2 mL PBS, CFSE with a final concentration of 1.5 µM was added, stained at room temperature for 10 min;

(4) 6 ml complete medium was added, placed on ice for 5 min, and centrifuged at 1000 rpm for 5 min; (5) the cells were resuspended with 1.2 ml complete medium, divided into four 96 wells, and antibody was added and incubated for 1 h; (6) M1 macrophage culture medium was sucked out, the stained Raji cells were added, and incubated for 3 h; (7) the phagocytosis of tumor cells by M1 macrophages under a fluorescence microscope was observed.

Figure 14:
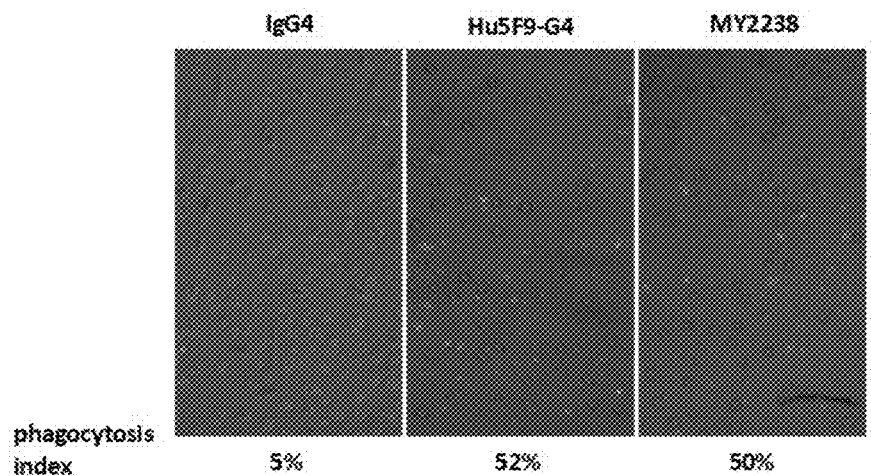
FIG. 14 is the detection of a humanized CD47 antibody Fc fusion protein-mediated macrophage phagocytosis of tumor cells. The results show that the MY2238 antibody can obviously promote the phagocytosis of Raji cells by macrophages, and the phagocytosis rate is about 50%, and its effect is similar to that of the Hu5F9-G4 product (Forty-Seven company) in clinical phase I.

As shown in FIG. 14, the MY2238 antibody can significantly promote the phagocytosis of Raji cells by macrophages, with a phagocytosis rate of about 50%, and its effect is similar to that of the Hu5F9-G4 product (FortySeven company) in clinical phase I.

Figure 15:
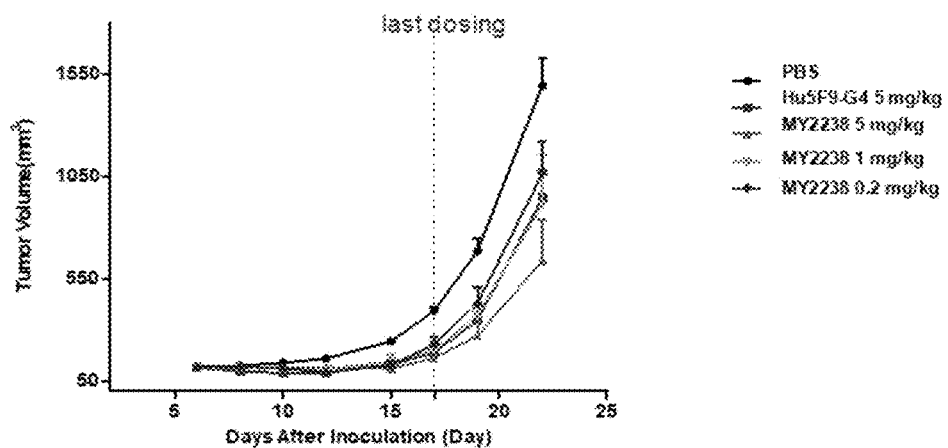
FIG. 15 shows the results of the drug efficacy of the humanized CD47 single domain antibody Fc fusion protein in a human ovarian cancer model. The results show that the candidate antibody MY2238 shows a good dose-dependent effect on tumor inhibition in this drug efficacy model. The drug efficacy (TGI=62%) of the candidate antibody MY2238 at the same dose is significantly better than that of the control antibody Hu5F9-G4, and the drug effect of MY2238 antibody 1 mg/kg (TGI=40%) is equivalent to that of control antibody Hu5F9-G4 5 mg/kg (TGI=42%).

Example 13: Efficacy of Humanized CD47 Single Domain Antibody Fc Fusion Protein in Human Ovarian Cancer Model SK-OV-3 cells were inoculated into BABL/C mice and divided into five groups after tumor formation for the administration (negative group: PBS, positive control group: 5 mg/kg Hu5F9-G4, experimental group: 5 mg/kg MY2238, 1 mg/kg MY2238, 0.2 mg/kg MY2238). Dosing frequency: once a day for 12 days. The experimental results are shown in FIG. 15: Candidate antibody MY2238 has a good dose-dependent effect on tumor inhibition in this drug efficacy model. At the same dose, the efficacy of candidate antibody MY2238 (TGI=62%) is significantly better than that of the control antibody Hu5F9-G4, and the efficacy of MY2238 antibody 1 mg/kg (TGI=40%) is equivalent to that of control antibody Hu5F9-G4 5 mg/kg (TGI=42%).

Example 14: Binding of Humanized CD47 Single Domain Antibody Fc Fusion Protein to Human Erythrocyte Cells (1) The control antibody Hu5F9-G4 was gradient diluted (5 µg/ml, 2.5 µg/ml, 1.25 µg/ml, 0.625 µg/ml, 0.3125 µg/ml, 0.15625 µg/ml, 0.078125 µg/ml, 0.039 µg/ml, 0.0195 µg/ml, 0.00975 µg/ml, 0.0049 µg/ml, 0.0024 µg/ml) and MY2238 was gradient diluted (40 µg/ml, 20 µg/ml, 10 µg/ml, 5 µg/ml, 2.5 µg/ml, 1.25 µg/ml, 0.625 µg/ml, 0.3125 µg/ml, 0.15625 µg/ml, 0.078125 µg/ml, 0.039 µg/ml, 0.0195 µg/ml); (2) The above 100 µL diluted antibody was incubated with $3\times10^5$ human erythrocytes respectively at 4° C. for 20 min (in this experiment, the peripheral blood of two people was taken at the same time and their erythrocytes were separated); (3) It was centrifuged at 3000 rpm, 4° C. for 4 min, supernatant was removed, 200 uL PBS/well was added, resuspended; (4) It was centrifuged at 3000 rpm and 4° C. for 4 min, and the anti-human Fc-FITC was diluted at 1:200 during the centrifugation process and placed on ice after preparation and kept in dark place. After centrifugation, the supernatant was removed and 100 uL/well was added, resuspended and incubated at 4° C. for 20 min; (5) 200 uL PBS/well was added to wash cells, centrifuged at 3000 rpm, 4° C. for 4 min, and supernatant was removed, and 200 uL PBS/well was added, resuspended, transferred to a flow tube and the FITC signal of each sample was tested on the machine.

Figure 16:
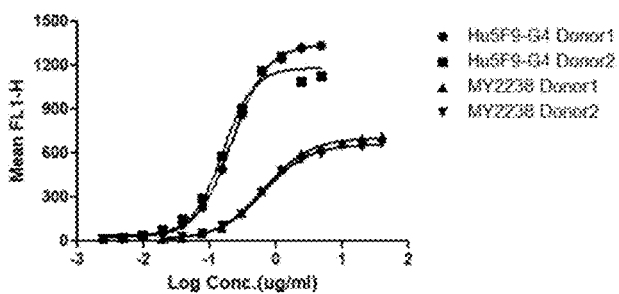
FIG. 16 shows the binding of humanized CD47 single domain antibody Fc fusion protein to human erythrocytes. The results show that the binding activity of candidate antibody MY2238 to CD47 on the surface of erythrocyte (Donor 1 EC50=0.6625 μg/mL, Donor 2 EC50=0.6443 μg/mL) is much lower than that of Hu5F9-G4 to erythrocyte (Donor 1 $EC_{50}$=0.2208 μg/mL, Donor 2 $EC_{50}$=0.1583 μg/mL).

The results are shown in FIG. 16: The binding activity of candidate antibody MY2238 to CD47 on the surface of erythrocyte (Donor 1 $EC_{50}$=0.6625 µg/mL, Donor 2 $EC_{50}$=0.6443 µg/mL) is much lower than that of Hu5F9-G4 to erythrocyte (Donor 1 $EC_{50}$=0.2208 µg/mL, Donor 2 $EC_{50}$=0.1583 µg/mL).

Example 15: Agglutination Reaction of Humanized CD47 Single Domain Antibody Fc Fusion Protein to Human Erythrocytes Due to the high expression of CD47 on the surface of erythrocytes, it will be easier to preferentially bind to the CD47 antibody drug and enrich the drug on the surface to play the role of "reservoir". Therefore, this situation is prone to anemia. After the drugs enters the body, it is necessary for them to break through the "absorption pool" effect of platelets on the CD47 antibody to reach the active site effectively and play their roles.

Humanized CD47 single domain antibody Fc fusion protein, positive control antibody (B6H12, sequence derived from patent of WO 2011143624 A2), positive control antibody (Hu5F9-G4), negative control (IgG4) were respectively diluted to 8000 nM, 2000 nM, 500 nM, 125 nM, 31.25 nM, 7.81 nM, 1.95 nM, 0 nM. 50 µL of the gradient diluted antibody was added to 50 µL of human erythrocyte suspension (2%) and placed at 37° C. overnight to observe the results.

Figure 17:
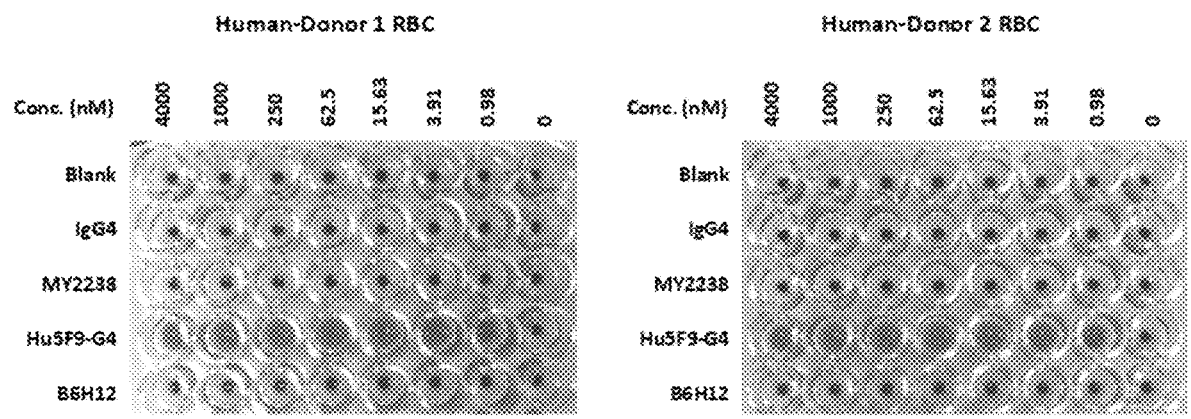
FIG. 17 is the result of agglutination effect of humanized CD47 single domain antibody Fc fusion protein on erythrocyte. The results show that the candidate antibody MY2238 cannot cause agglutination of human erythrocyte, while the control antibody Hu5F9-G4 can significantly cause the erythrocyte agglutination.

The results as shown in FIG. 17 show that the humanized CD47 single domain antibody Fc fusion protein does not cause agglutination reaction of human erythrocyte. The experimental results of the control antibodies (B6H12 and Hu5F9-G4) are consistent with the results reported by Penka S. Petrova et al., 2016, Clin. Cancer. Res. 23 (4).

Example 16: Toxicological Study of Humanized CD47 Single Domain Antibody Fc Fusion Protein in Cynomolgus Monkey Since the CD47 antibody can bind to CD47 on the surface of erythrocytes, there may be a risk of causing side effects such as anemia, so that it is necessary to explore the toxic and side effects of the candidate antibody in animals. Four cynomolgus monkeys were injected with antibodies under four conditions: (1) single injection of 10 mg/kg; (2) single injection of 30 mg/kg; (3) injection of 3 mg/kg in the first week, and injection of 60 mg/kg in the second week; (4) 3 mg/kg injection in the first week and 200 mg/kg injection in the second week. Then various physiological indicators of cynomolgus monkeys were regularly observed and tested.

Figure 18:
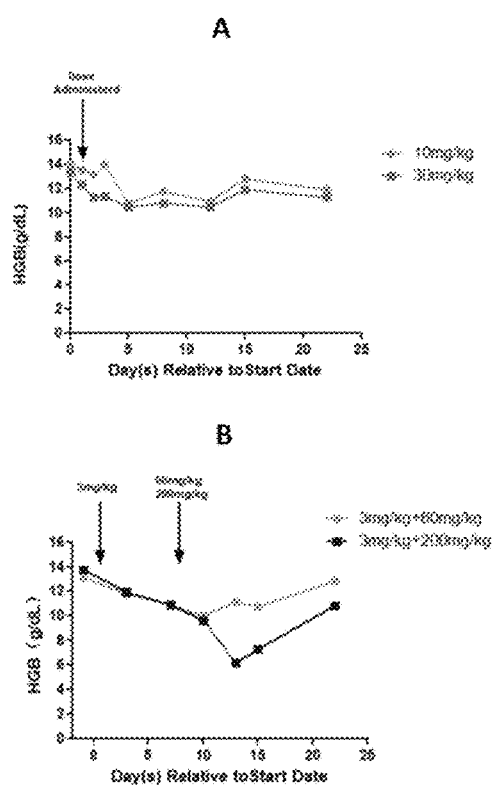
FIG. 18 is the toxicological results of the humanized CD47 single domain antibody Fc fusion protein in cynomolgus monkeys. The results show that different doses of the candidate antibody MY2238 does not cause significant physiological toxicity in cynomolgus monkeys. Even under the injection conditions of high-dose 60 mg/kg and 200 mg/kg, after the level of hemoglobin in the cynomolgus monkey is reduced, it still returns to normal levels, and there is no physiological abnormalities during the research. Therefore, the candidate antibody MY2238 has excellent in vivo safety.

The results are shown in FIG. 18: at a single dose of 10 mg/kg, the candidate antibody MY2238 reduces hemoglobin from 140 g/L to a minimum of 108 g/L, with a decrease of 22.85%; at a single dose of 30 mg/kg, hemoglobin was decreased from 134 g/L to a minimum of 105 g/L, with a decrease of 21.64%. According to Jie Liu, Lijuan Wang et al., Plos One.2015 Sep. 21; 10 (9): e0137345, the reported literature indicates that at a dose of 30 mg/kg, Hu5F9-G4 reduces hemoglobin from 125 g/L to a minimum of 70 g/L, with a decrease of about 44%. This shows that MY2238 has a better security. In addition, under the conditions of high doses of 60 mg/kg and 200 mg/kg, hemoglobin in cynomolgus monkeys is also returned to normal levels after being reduced, and no physiological abnormalities is occurred during the study. Therefore, it is shown that the candidate antibody MY2238 has an excellent in vivo safety.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A complementarity determining region CDR region of an anti-CD47 single domain antibody VHH chain, wherein the complementarity determining region CDR of the VHH chain is composed of CDR1 as shown in SEQ ID NO: 5, CDR2 as shown in SEQ ID NO: 6, and CDR3 as shown in SEQ ID NO: 7.

2. A VHH chain of an anti-CD47 single domain antibody, wherein the VHH chain comprises a framework region FR and the complementarity determining region CDR of claim 1, wherein the framework region FR consists of:

(a) FR1 as shown in SEQ ID NO: 1, FR2 as shown in SEQ ID NO: 2, FR3 as shown in SEQ ID NO: 3, and FR4 as shown in SEQ ID NO: 4; or (b) FR1 as shown in SEQ ID NO: 10, FR2 as shown in SEQ ID NO: 11, FR3 as shown in SEQ ID NO: 12, and FR4 as shown in SEQ ID NO: 13.

3. An anti-CD47 single domain antibody, which is a single-domain antibody directed against the CD47 epitope and has a VHH chain of the amino acid sequence as shown in SEQ ID NO: 8 or SEQ ID NO: 14.

4. An anti-CD47 single domain antibody Fc fusion protein, wherein the structure of the fusion protein from N-terminus to C-terminus is shown as formula Ia or Ib:

A-L-B (Ia);

B-L-A (Ib)

wherein
A is the anti-CD47 single domain antibody of claim 3;
B is a Fc fragment of IgG; and
L is none or a flexible linker.

5. A polynucleotide encoding a protein selected from the group consisting of: the CDR region of claim 1, the VHH chain of the anti-CD47 single domain antibody of claim 2, the anti-CD47 single domain antibody of claim 3, and the anti-CD47 single domain antibody Fc fusion protein of claim 4.

6. The polynucleotide of claim 5, wherein the polynucleotide has a nucleotide sequence as shown in SEQ ID NOs: 9, 15, or 17.

7. An expression vector containing the polynucleotide of claim 5.

8. A host cell containing the expression vector of claim 7, or with the polynucleotide of claim 5 integrated into a genome thereof.

9. A method for producing an anti-CD47 single domain antibody or an Fc fusion protein thereof, comprising the steps of:
  (a) cultivating the host cell of claim 8 under conditions suitable for the production of a single-domain antibody or a Fc fusion protein thereof, thereby obtaining a culture containing the anti-CD47 single domain antibody or the Fc fusion protein thereof; and
  (b) isolating or recovering the anti-CD47 single domain antibody or the Fc fusion protein thereof from the culture.

10. An immunoconjugate containing:
  (a) the VHH chain of the anti-CD47 single domain antibody of claim 2, or the anti-CD47 single domain antibody of claim 3, or the anti-CD47 single domain antibody Fc fusion protein of claim 4; and
  (b) a coupling moiety selected from the group consisting of: a detectable marker, drug, toxin, cytokine, radionuclide, and enzyme.

11. A method of detecting CD47 within a subject comprising obtaining a sample from the subject and administering to said sample an anti-CD47 single domain antibody of claim 2.

12. A method of detecting CD47 within a subject comprising obtaining a sample from the subject and administering to said sample an anti-CD47 single domain antibody of claim 3.

13. A method of detecting CD47 within a subject comprising obtaining a sample from the subject and administering to said sample an anti-CD47 single domain antibody of claim 4.

14. A method of treating cancer within a subject comprising administering to said subject an anti-CD47 single domain antibody of claim 2, wherein the single domain antibody has antitumor activity.

15. A method of treating cancer within a subject comprising administering to said subject an anti-CD47 single domain antibody of claim 3, wherein the single domain antibody has antitumor activity.

16. A method of treating cancer within a subject comprising administering to said subject an anti-CD47 single domain antibody of claim 4, wherein the single domain antibody has antitumor activity.

* * * * *